US009493539B2

(12) United States Patent
Hill et al.

(10) Patent No.: US 9,493,539 B2
(45) Date of Patent: Nov. 15, 2016

(54) PEPTIDES ASSOCIATED WITH HLA-DR MHC CLASS II MOLECULES INVOLVED IN AUTOIMMUNE DISEASES

(75) Inventors: Jonathan Hill, London (CA); Ewa Cairns, London (CA); David Bell, London (CA)

(73) Assignee: LONDON HEALTH SCIENCES CENTRE RESEARCH INC., London, Ontario (CA)

( * ) Notice: Subject to any disclaimer, the term of this patent is extended or adjusted under 35 U.S.C. 154(b) by 1684 days.

(21) Appl. No.: 10/548,258

(22) PCT Filed: Mar. 5, 2004

(86) PCT No.: PCT/CA2004/000337
§ 371 (c)(1),
(2), (4) Date: Oct. 27, 2006

(87) PCT Pub. No.: WO2004/078098
PCT Pub. Date: Sep. 16, 2004

(65) Prior Publication Data
US 2007/0292347 A1    Dec. 20, 2007

Related U.S. Application Data

(60) Provisional application No. 60/452,522, filed on Mar. 7, 2003.

(51) Int. Cl.
*C07K 14/74* (2006.01)
*C07K 14/47* (2006.01)
*A61K 38/00* (2006.01)

(52) U.S. Cl.
CPC ..... *C07K 14/70539* (2013.01); *C07K 14/4713* (2013.01); *A61K 38/00* (2013.01); *Y10S 435/81* (2013.01)

(58) Field of Classification Search
None
See application file for complete search history.

(56) References Cited

U.S. PATENT DOCUMENTS 4,281,061 A    7/1981 Zuk et al.
8,198,401 B2   6/2012 Hill et al.

OTHER PUBLICATIONS

Union, A., et al. Arthit. Rheum. 2002;46(5):1185-1195.*
Bas et al., "Association of rheumatoid factors and anti-flaggrin antibodies with severity of erosions in rheumatoid arthritis", Rheumatology, 39, pp. 1082-1088 (2000).
Goldbach-Mansky et al., "Rheumatoid arthritis associated autoantibodies in patients with synovitis of recent onset", Arthritis Res., 2, pp. 236-243 (2000).
Gregersen et al., "The Shared Epitope Hypothesis. An Approach to Understanding the Molecular Genetics of Susceptibility to Rheumatoid arthritis", Arthritis Rheum., 30(11), pp. 1205-1213 (1987).
Hammer et al., "Peptide Binding Specificity of HLA-DR4 Molecules: Correlation with Rheumatoid Arthritis Association", J. Exp. Med., 181, pp. 1847-1855 (1995).
Hammer et al., "Precise Prediction of Majour Histocompatibility Complex Class II-Peptide Interaction Based on Peptide Side Chain Scanning", J. Exp. Med., 180, pp. 2353-2358 (1994).
Hill et al., "Cutting edge: The Conversion of Arginine to Citrulline Allows for a High Affinity Peptide Interaction with the Rheumatoid Arthritis-Associated HLA-DRB1*0401 MNC Class II Molecule", The Journal of Immunology, 171, pp. 538-541 (2003).
Masson-Bessiere et al., "The Major Synovial Targets of the Rheumatoid arthritis-Specific Antifilaggrin Autoantibodies Are Deiminated Forms of the α- and β-Chains of Fibrin 1," The Journal of Immunology, 166, pp. 4177-4184 (2001).
Menard et al., "Insights into rheumatoid arthritis derived from the Sa immune system", Arthritis Res., 2(6), pp. 429-432 (2000).
Reviron et al., "Influence of Shared Epitope-Negative HLA-DRB1 Alleles on Genetic Susceptibility to Rheumatoid Arthritis", Arthritis Rheum., 44(3) pp. 535-540 (2001).
Sturniolo et al., "Generation of tissue-specific and promiscuous HLA ligand databases using DNA microarrays and virtual HLA class II matrices", Nat. Biotechnol., 17, pp. 555-561 (1999).
van Venrooij et al., "Citrullination: a small change for a protein with great consequences for rheumatoid arthritis", Arthritis Res., 2(4), pp. 249-251 (2000).
Zhou et al., "Autoantigenic posttranslational modifications of proteins: does it apply to rheumatoid arthritis?", Curr. Opin. Rheumatol., 14, pp. 250-253 (2002).
Hill et al., "Cutting Edge: The Conversion of Arginine to Citrulline Allows for a High-Affinity Peptide Interaction with the Rheumatoid Arthritis-Associated HLA-DRB1 *0401 MHC Class II Molecule," *J. Immunol.*, 2003, 171: 538-541.
Ito et al., "HLA-DR4-IE Chimeric Class II Transgenic, Murine Class II-Deficient Mice Are Susceptible to Experimental Allergic Encephalomyelitis," *J. Exp. Med.*, 1996, 183: 2635-2644.
Van Venrooij et al., "Citrullination: a small change for a protein with great consequences for rheumatoid arthritis," *Arthritis Res.*, 2000, 2: 249-251.
Schellekens et al., "The Diagnostic Properties of Rheumatoid Arthritis Antibodies Recognizing a Cyclic Citrullinated Peptide," Arthritis Rheum., 2000, 43(1):155-163.
Hagiwara et al., "Deimination of Arginine Residues in Nucleophosmin/B23 and Histones in HL-60 Granulocytes," *Biochem. Biophys. Res. Commun.*, 2002, 290(3): 979-983.
Inagaki et al., "$Ca^{2+}$—dependent Deimination-induced Disassembly of Intermediate Filaments Involves Specific Modification of the Amino-terminal Head Domain," *J. Biol. Chem.*, 1989, 264(30): 18119-18127.
Schellekens et al., "Citrulline is an Essential Constituent of Antigenic Determinants Recognized by Rheumatoid Arthritis-specific Autoantibodies," *J. Clin. Invest.*, 1998, 101(1): 273-281.
Tranquill et al., "Enhanced T Cell Responsiveness to Citrulline-containing Myelin Basic Protein in Multiple Sclerosis Patients," *Mult. Scler.*, 2000, 6(4): 220-225.
James, et al., "HLA-DR1001 Presents 'Altered-Self'Peptides Derived From Joint-Associated Proteins by Accepting Citruline in Three of its Binding," Arthritis & Rheumatism (2010), 62 (10): 2909-2918.

* cited by examiner

*Primary Examiner* — Gerald R Ewoldt
(74) *Attorney, Agent, or Firm* — Knobbe, Martens, Olson & Bear, LLP

(57) ABSTRACT

Antigenic peptides that bind to MHC Class II molecules with the shared epitope referred to as HLA-DR molecules are disclosed. More specifically, are citrullinated antigenic peptides having an increased affinity for HLA-DR molecules and associated with Rheumatoid arthritis. These novel peptides provide the basis for new methods of diagnosis and treatment of Rheumatoid arthritis.

8 Claims, 10 Drawing Sheets

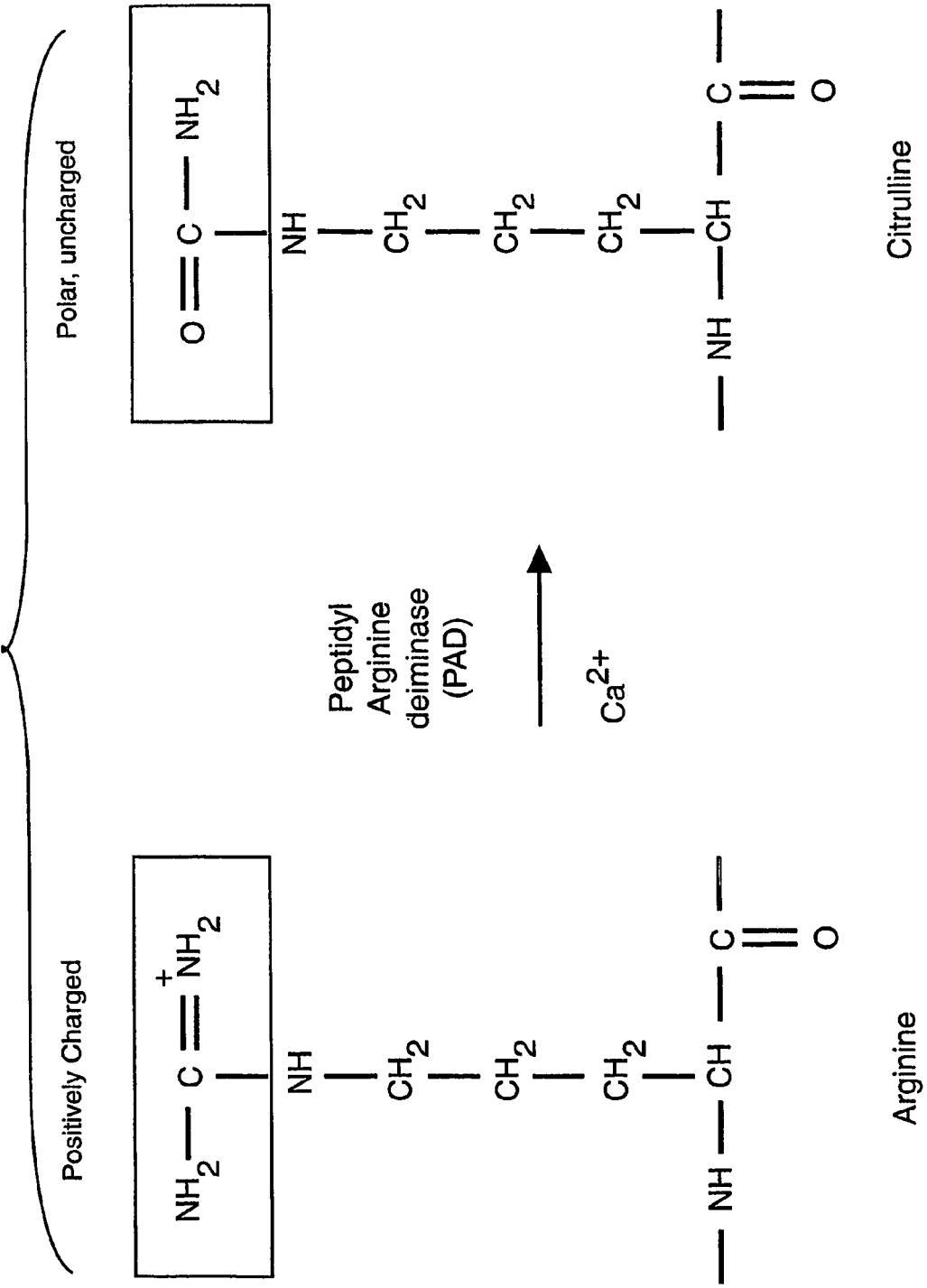

Clinical appearance of Cit-Fib induced arthritis. DR4 tg mice were immunized and boosted with either adjuvant alone (A), fibrinogen (B), or citrullinated fibrinogen (C). Signs of arthritis in citrullinated fibrinogen immunized mice were evident 10 wks after immunization. Swelling did not occur at any time point in control mice (A and B).

H&E stained sections from the tibiotalor joint of an arthritic Cit-Fib immunized mouse (A) and an unaffected mouse immunized with fibrinogen (C). Pannus formation is highlighted by a box in A with a higher magnification shown in B.

PEPTIDES ASSOCIATED WITH HLA-DR MHC CLASS II MOLECULES INVOLVED IN AUTOIMMUNE DISEASES

FIELD OF THE INVENTION

The invention relates to novel antigenic peptides that bind to MHC class II molecules with the shared epitope referred to as HLA-DR molecules. More specifically, the invention is directed to citrullinated antigenic peptides that have an increased affinity for HLA-DR molecules and are associated with certain autoimmune diseases. As such these novel peptides provide the basis for new methods of diagnosis and treatment of autoimmune disorders in subjects having MHC class II molecules with the shared epitope, such autoimmune disorders including rheumatoid arthritis and multiple sclerosis.

BACKGROUND OF THE INVENTION

Throughout this application, various references are cited in parentheses to describe more fully the state of the art to which this invention pertains. The disclosure of these references are hereby incorporated by reference into the present disclosure.

Rheumatoid arthritis (RA) is a prevalent autoimmune disease characterized by synovial inflammation and pannus formation which can lead to cartilage and bone degradation. This debilitating condition affects nearly 1% of the population. Genetic susceptibility to this disease is associated with MHC class II molecules that contain an amino acid motif known as the shared epitope (SE) and are designated as HLA-DR molecules (Gregersen, P. K., J. Silver, R. J. Winchester. 1987. The shared epitope hypothesis. An approach to understanding the molecular genetics of susceptibility to rheumatoid arthritis. *Arthritis Rheum.* 30:1205, Zhou, Z., H. A. Menard. 2002. Autoantigenic posttranslational modifications of proteins: does it apply to rheumatoid arthritis? *Curr. Opin. Rheumatol.* 14:250). The shared epitope, expressed by the amino acid residues Q/R, K/R, R, A, A, is positively charged and forms one of the major peptide anchoring pockets (known as P4) of the MHC class II molecules.

Previous reports have suggested that a distinct feature of a putative pathogenic peptide involved in RA may be the presence of the negatively charged side-chain at P4 (interacting with the shared epitope) (Hammer J., Gallazzi F., Bono E., Karr R. W., Guenot J., Valsasnini P., Nagy Z. A., Sinigaglia F. 1995. Peptide binding specificity of HLA-DR4 molecules: correlation with rheumatoid arthritis association. *J. Exp. Med.* 181:1847). This is based on the fact that certain MHC class II molecules, HLA-DR*0401 and HLA-DR*0404 (allelic variants) have a substantially higher affinity for aspartic and glutamic acid amino acid residues at the P4 pocket than the RA non-associated HLA-DR*0402 molecule. However, after analysis of multiple DRB1 pocket profiles it can be found that some RA non-associated alleles have a higher affinity for negatively charged amino acids at their P4 pockets than even HLA-DR *0101, HLA-DR *0401, and HLA-DR *0404, such as HLA-DR *0301 (Sturniolo T, Bono E, Ding J, Raddrizzani L, Tuereci O, Sahin U, Braxenthaler M, Gallazzi F, Protti M P, Sinigaglia F, Hammer J. 1999. Generation of tissue-specific and promiscuous HLA ligand databases using DNA microarrays and virtual HLA class II matrices. *Nat. Biotechnol.* 17:555). Some MHC molecules appear to be protective against disease (e.g. HLA-DR *0402), rather than simply non-associated, suggesting that a passive role for these alleles in peptide binding may not occur (Reviron, D., A. Perdriger, E. Toussirot, D. Wendling, N. Balandraud, S. Guis, G. Semana, P. Tiberghien, P. Mercier, J. Roudier. 2001. Influence of shared epitope-negative HLA-DRB1 alleles on genetic susceptibility to rheumatoid arthritis. *Arthritis Rheum.* 44:535). Instead, protective alleles (MHC molecules) may bind a putative pathogenic peptide with high enough affinity as to induce negative T cell selection, or to establish peripheral tolerance.

The MHC class II molecules with the shared epitope may participate in disease pathogenesis by selectively binding arthritogenic peptides for presentation to autoreactive CD4$^+$ T cells. Currently, the nature of the autoantigen responsible for RA is not known. While many candidate autoantigens have been investigated in the context of RA associated MHC, a common disease specific target of the CD4$^+$ T cell and B cell immune response remains elusive. Recent studies have shown that RA patients have a subset of IgG autoantibodies that are both sensitive and specific (>90%) for the diagnosis of RA. The target of these autoantibodies is citrulline, a post-translationally modified arginine (deiminated arginine) found within the context of certain protein/peptide sequences (van Venrooij, W. J., G. J. Pruijn. 2000. Citrullination: a small change for a protein with great consequences for rheumatoid arthritis. *Arthritis Res.* 2:249). Citrulline is the essential antigenic epitope target of anti-perinuclear, anti-keratin, anti-filaggrin, anti-cyclic citrullinated peptide, and anti-Sa antibodies (van Venrooij, W. J., G. J. Pruijn. 2000. Citrullination: a small change for a protein with great consequences for rheumatoid arthritis. *Arthritis Res.* 2:249; Zhou, Z., H. A. Menard. 2002. Autoantigenic posttranslational modifications of proteins: does it apply to rheumatoid arthritis? *Curr. Opin. Rheumatol.* 14:250). These antibodies target citrulline within a number of different proteins, the joint derived targets appears to be vimentin and fibrin(ogen) (Menard, H. A., E. Lapointe, M. D. Rochdi, Z. J. Zhou. 2000. Insights into rheumatoid arthritis derived from the Sa immune system. *Arthritis Res.* 2:429; Christine Masson-Bessiere et al., 2001. The Major Synovial Targets of the Rheumatoid arthritis-Specific Antifilaggrin Autoantibodies Are Deiminated Forms of the α and β Chains of Fibrin 1 *The Journal of Immunology* 166: 4177-4184). It is also observed that anti-citrulline antibody production is significantly associated with the presence of the MHC shared epitope in R A patients (Goldbach-Mansky R, Lee J, McCoy A, Hoxworth J, Yarboro C, Smolen J S, Steiner G, Rosen A, Zhang C, Menard H A, Zhou Z J, Palosuo T, Van Venrooij W J, Wilder R L, Klippel J H, Schumacher H R Jr, El-Gabalawy H S. 2000. Rheumatoid arthritis associated autoantibodies in patients with synovitis of recent onset. *Arthritis Res.* 2:236; Bas S, Perneger T V, Mikhnevitch E, Seitz M, Tiercy J M, Roux-Lombard P, Guerne P A. 2000. Association of rheumatoid factors and anti-filaggrin antibodies with severity of erosions in rheumatoid arthritis. *Rheumatology (Oxford).* 39: 1082).

The Applicant has now demonstrated that a unique interaction exists between the shared epitope of MHC class II molecules and the amino acid citrulline. This interaction is involved in generating T cell responses and subsequently B cell responses to these citrullinated antigens in autoimmune diseases where a patient expresses the shared epitope. Furthermore, the Applicant has now identified novel citrullinated antigens that evoke a T cell response leading to inflammation and the development of autoimmune disease such as rheumatoid arthritis as well as multiple sclerosis.

SUMMARY OF THE INVENTION

The Applicant has identified novel citrullinated peptide antigens that evoke a T cell response via binding to the positively charged P4 pocket (the shared epitope) of MHC class II molecules. The Applicant has demonstrated that the modification of a positively charged amino acid to that of citrulline, an uncharged polar amino acid, leads to the increased affinity for the antigen to MHC class II molecules with the shared epitope. This increased antigen affinity leads to T cell activation which in turn mediates an inflammatory reaction resulting in the development of an autoimmune disorder, such as rheumatoid arthritis, in a subject.

As such, the present invention encompasses the use of the citrullinated peptides of the invention in a variety of diagnostic and therapeutic approaches to diagnose or treat autoimmune disease characterized by the binding of a citrullinated peptide with MHC class II molecules with the shared epitope leading to T cell activation. In aspects of the invention, such autoimmune disorders may include for example rheumatoid arthritis (RA) and multiple sclerosis (MS).

The T cell responses to citrulline containing peptides (via conversion of arginine to citrulline, a process which replaces the charged imino side-chain group with an uncharged carbonyl) were studied in HLA-DRB1*0401 transgenic (DR4-IE tg) mice. The work demonstrated that the conversion of arginine to citrulline at the peptide side-chain position interacting with the shared epitope significantly increases peptide-MHC affinity and leads to the activation CD4+ T cells in the DR4-IE tg mice. This post-translational modification was necessary to elicit a CD4+ T cell response to these peptides in DR4-IE tg mice. Peptide affinity for a number of HLA alleles was assessed and showed that only MHC class II molecules with the shared epitope had an increased affinity for a citrulline containing peptide.

Taken together, the Applicant has identified a novel peptide-MHC interaction that helps to explain the molecular basis of disease associated HLA alleles in RA and more specifically reveals that MHC class II molecules with the shared epitope are involved in initiating an autoimmune response to citrullinated self-antigens in RA patients. As citrullinated myelin basic protein (MBP) T cell responses have previously been observed, the present invention also encompasses diagnostic and therapeutic treatments for multiple sclerosis (MS) for subjects expressing the MHC class II shared epitope.

The invention encompasses all MHC Class II molecules having a shared epitope sequence such that there is an increase in peptide affinity with citrulline is present versus arginine. Such MHC molecules may include but are not limited to HLA-DRB1*0401, HLA-DRB1*0404, HLA-DRB1*0405, HLA-DRB1*0408, HLA-DRB1*0409, HLA-DRB1*0410, HLA-DRB1*1001, HLA-DRB1*0101, HLA-DRB1*0102, HLA-DRB1*1402, HLA-DRB1*1406, HLA-DRB1*1409 and HLA-DRB4.

With the knowledge that citrullinated peptides act as arthritogenic antigens leading to T cell activation and resultant disease, novel and improved methods for diagnosis of autoimmune disorders characterized by the binding of citrullinated peptide antigens that bind to the shared epitope of any MHC class II molecule leading to a T cell activation and an autoimmune response, such as in RA and MS, involving this activation mechanism are now made available as well as the predisposition to developing such autoimmune disorders including RA and MS, are now made available.

Novel therapeutic approaches to treat autoimmune disorders as characterized supra, including RA and MS, are now also made available. Such novel approaches for treatment of autoimmune diseases may in aspects involve blocking the conversion of arginine to citrulline, thus inhibiting/reducing the production of citrullinated peptide antigens causative of RA or MS. Such blocking or inhibition may in one aspect involve blocking the expression of peptidylarginine deiminase (PAD) enzyme and thus the generation of citrullinated peptide antigens. This provides for a more cost-effective novel therapy for RA and MS that can potentially block disease progression at an earlier stage. In other aspects, blocking of the PAD enzyme may involve the use of small molecules inhibitory to the action of the PAD enzyme.

According to an aspect of the invention are novel citrullinated peptides that bind with high affinity to MHC class II molecules with the shared epitope said peptides evoking a T cell response in the blood of a patient with an autoimmune disorder or a patient at risk for developing an autoimmune disorder. In aspects of the invention, the T cell is a CD4+ T cell. In further aspects of the invention, the autoimmune disorder may be RA or MS.

According to another aspect of the invention are novel citrullinated peptides that bind with high affinity to MHC class II molecules with the shared epitope said peptides evoking a T cell response in the blood of a patient with RA, or a patient at risk for developing RA.

According to a further aspect of the invention are novel citrullinated peptides that bind with high affinity to MHC class II molecules with the shared epitope, said peptides evoking a T cell response in the blood of a RA patient, or a patient at risk for developing RA, wherein said T cell is a CD4+ T cell.

According to yet a further aspect of the invention is a novel citrullinated peptide, said peptide being produced by the action of peptidylarginine deiminase on an endogenous or exogenous protein, wherein said citrullinated peptide binds to MHC class II molecules having the shared epitope.

According to yet another aspect of the invention is a citrullinated peptide that binds with high affinity to MHC class II molecules with the shared epitope, said peptide evoking a T cell response in the blood of a RA patient, or a patient at risk for developing RA, said peptide being selected from the group consisting of citrullinated fibrinogen peptides and citrullinated vimentin peptides. In aspects, the fibrinogen and vimentin peptides for use in the invention and the target of citrullination, are selected from the known human sequences for each of these proteins. Furthermore, the fibrinogen human protein sequences may be further selected from alpha/alpha-e chain precursor protein, beta chain precursor protein, alpha-A chain precursor protein, gamma chain precursor protein or the mature forms of these chains. In other aspects, the citrullinated peptide may be a full length fibrinogen or vimentin protein. Protein sequences encompassed by the present invention may be found in Genbank and SWISS-PROT as is understood by one of skill in the art.

According to another aspect of the invention is a peptide containing a deiminated arginine, the peptide being from at least about 9 amino acids in length, the peptide binding with high affinity to MHC class II molecules with the shared epitope, wherein the peptide evokes a T cell response in the blood of a RA patient, or a patient at risk for developing RA.

According to still another aspect of the invention is a citrullinated peptide that binds with high affinity to MHC class II molecules with the shared epitope, said peptide evoking a T cell response in the blood of a RA patient, or a patient at risk for developing RA, said peptide comprising at least one of the amino acid sequences selected from the group consisting of: SAVRACitSSVPGVR (SEQ ID NO. 1); FSMCitIVCLV (SEQ ID NO. 2); WECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); VETCitDGQVI (SEQ ID NO. 37) and functional analogues thereof.

According to still a further aspect of the invention is a citrullinated peptide that binds with high affinity to MHC class II molecules with the shared epitope, said peptide evoking a T cell response in the blood of a RA patient, or a patient at risk for developing RA, said peptide being selected from the group consisting of: SAVRACitSSVPGVR (SEQ ID NO. 1); FSMCitIVCLV (SEQ ID NO. 2); WECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); VETCitDGQVI (SEQ ID NO. 37) and functional analogues thereof.

According to other aspects of the invention, the citrullinated peptide of the invention may be an artificial sequence that contains multiple citrulline residues and generates anti-citrulline antibodies in vivo.

In one aspect, is a citrullinated peptide that binds with high affinity to MHC class II molecules with the shared epitope, said peptide generating anti-citrulline antibodies in vivo in a mammal, said peptide having the formula:

Cit-Cit-X-Cit-G-Cit-Cit-Z-Cit-Cit-B-Cit-Cit (SEQ ID NO. 38), wherein X is selected from Y, F, W, I, L, M and V; Z is selected from A, D, I, N, P, S, T, V; and B is selected from A, G, H, Q, S, T and V.

In aspects of the invention, this peptide may have cysteines added to one or both ends of the peptide to circularize by means of disulfide bond formation. In further aspects of the invention the peptide comprises Cit-Cit-Y-Cit-G-Cit-Cit-S-Cit-Cit-S-Cit-Cit (SEQ ID NO. 39). In still further aspects, the citrullinated peptide may include charged amino acid at the beginning and/or end of the sequence of SEQ ID NO. 38 or 39. Such charged amino acids may be selected from arginine, lysine, asparagine, aspartic acid, glutamic acid and glutamate. In further aspects, the peptide may be circularized in order to increase its immunological affinity.

According to another aspect of the present invention is a citrullinated myelin basic protein (MBP) peptide that binds with high affinity to MHC class II molecules with the shared epitope, said peptide evoking a T cell response in the blood of a MS patient, or a patient at risk for developing MS, said peptide being selected from the group consisting of FLPCitHRDTG (SEQ ID NO. 40), VTPCitTPPPS (SEQ ID NO. 41); YGGCitASKYK (SEQ ID NO. 42) and LGGCitDSRSG (SEQ ID NO. 43).

According to another aspect of the present invention is a citrullinated glial fibrillary acid protein (GFAP) peptide that binds with high affinity to MHC class II molecules with the shared epitope, said peptide evoking a T cell response in the blood of a MS patient, or a patient at risk for developing MS, said peptide being selected from the group consisting of MERCitRITSA (SEQ ID NO. 44), LPTCitVDFSL (SEQ ID NO. 45), LNDCitFASYI (SEQ ID NO. 46), LRLCitLDQLT (SEQ ID NO. 47), LQICitETSLD (SEQ ID NO. 48) and VEMCitDGEVI (SEQ ID NO. 49).

According to another aspect of the present invention is a peptide that is citrullinated in neutrophils and as such, may be used in the diagnostically or in the treatment of rheumatoid arthritis, said peptides being selected from the group consisting of: nucleophosmin/B23, Histone H2A, Histone H4 and Histone H3 wherein said peptide contains one or more citrulline residues.

According to another aspect of the present invention are citrullinated peptides selected from the group consisting of: LSLRTVSLG (SEQ ID NO. 50); WLRLKCGS (SEQ ID NO. 51); MSGRGKQGG (SEQ ID NO. 52); MSGRGKQGG (SEQ ID NO. 53); IIPRHLQLA (SEQ ID NO. 54); LAIRNDEEL (SEQ ID NO. 55); LLGRVTIAQ (SEQ ID NO. 56); MSGRGKGGK (SEQ ID NO. 57); LARRGGVKR (SEQ ID NO. 58); VALREIRRY (SEQ ID NO. 59); LLIRKLPFQ (SEQ ID NO. 60) and LARRIRGER (SEQ ID NO. 61), wherein said "R" arginine residue may be converted to citrulline by the action of PAD. Such peptides may be used in various assays such as to measure T cell reactivity as an indication of rheumatoid arthritis.

According to yet another aspect of the present invention is a method for detecting anti-citrulline antibodies in a sample from a subject, said method comprising;
    contacting a sample from a subject with a peptide of any one of SEQ ID NO. 40-48;
    detecting the binding of said peptide to an anti-citrulline antibody in said sample.

According to yet another aspect of the present invention is a method for detecting anti-citrulline antibodies in a sample from a subject, said method comprising;
    contacting a sample from a subject with a peptide having the formula:
    Cit-Cit-X-Cit-G-Cit-Cit-Z-Cit-Cit-B-Cit-Cit (SEQ ID NO. 38), wherein X is selected from Y, F, W, I, L, M and V;

Z is selected from A, D, I, N, P, S, T, V; and B is selected from A, G, H, Q, S, T and V; and detecting the binding of said peptide to an anti-citrulline antibody in said sample. The method useful in the diagnosis of RA. In aspects, the sample is a peripheral blood sample from a subject.

According to still another aspect of the invention is a method for diagnosing an autoimmune disorder in a subject, said method comprising:

contacting a sample taken from said subject with a peptide having the formula:

Cit-Cit-X-Cit-G-Cit-Cit-Z-Cit-Cit-B-Cit-Cit (SEQ ID NO. 38), wherein X is selected from Y, F, W, I, L, M and V; Z is selected from A, D, I, N, P, S, T, V; and B is selected from A, G, H, Q, S, T and V; and detecting the binding of said peptide to an anti-citrulline antibody in said sample; wherein binding is indicative of an autoimmune disorder. In aspects such an autoimmune disorder may be selected from RA and MS.

According to another aspect of the invention is a method for diagnosing MS in a subject, said method comprising:

contacting a sample taken from said subject with a citrullinated MBP peptide; and detecting the binding of said peptide to an anti-citrulline antibody in said sample; wherein binding is indicative of a diagnosis of MS.

Also within the scope of the invention are functional analogues of any of the peptides of the invention as well as multimers of the peptides according to the invention such as for example a dimer or trimer of the peptides according to the invention. A multimer according to the invention can either be a homomer, consisting of a multitude of the same peptide, or a heteromer consisting of different peptides. The characteristic amino acid sequences of the peptides according to the invention can be flanked by random amino acid sequences. Preferred are flanking sequences that have a stabilizing effect on the peptides, thus increasing their biological availability.

It is understood by one of skill in the art that certain of the peptide amino acid sequences listed supra have additional arginines within the sequence that may be converted to citrulline.

According to another aspect of the present invention is a composition comprising a citrullinated peptide that binds with high affinity to MHC class II molecules with the shared epitope, and is capable of evoking a T cell response in the blood of a RA patient, or a patient at risk for developing RA and a pharmaceutically acceptable carrier. The citrullinated peptide may be selected from the group consisting of SAVRACitSSVPGVR (SEQ ID NO. 1); FSMCitIVCLV (SEQ ID NO. 2); VVECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); VETCitDGQVI (SEQ ID NO. 37); Cit-Cit-X-Cit-G-Cit-Cit-Z-Cit-Cit-B-Cit-Cit (SEQ ID NO. 38, wherein X is selected from Y, F, W, I, L, M and V; Z is selected from A, D, I, N, P, S, T, V; and B is selected from A, G, H, Q, S, T and V; and Cit-Cit-Y-Cit-G-Cit-Cit-S-Cit-Cit-S-Cit-Cit (SEQ ID NO. 39).

According to another aspect of the present invention is a composition comprising a citrullinated peptide that binds with high affinity to MHC class II molecules with the shared epitope, and is capable of evoking a T cell response in the blood of a MS patient, or a patient at risk for developing MS and a pharmaceutically acceptable carrier. The citrullinated peptide may be selected from any one of the peptides represented by SEQ ID NO. 40-48.

The invention also provides use of any of the citrullinated peptide antigens disclosed herein for the preparation of a diagnostic means for use in a method of diagnosing an autoimmune disorder such as RA or MS, or susceptibility to an autoimmune disorder such as RA or MS, in an individual, the method comprising determining whether T cells of the individual recognize the citrullinated peptide antigen as bound to the MHC class II shared epitope positive cell, wherein recognition by the T cells indicates that the individual has, or is susceptible to, an autoimmune disorder.

According to still another aspect of the present invention is a diagnostic method for the detection of autoreactive T cells which are reactive with a citrullinated antigen bound to MHC class II shared epitope positive cell, said method comprising;

incubating an isolated sample of peripheral blood mononuclear cells from a patient with one or more citrullinated peptide antigens;

detecting the response of T cells, indicating the presence of activated autoreactive T cells in said patient.

In aspects the peptide antigens may be selected from any one of SEQ ID NO. 1-60.

According to another aspect of the present invention is a test kit for the detection of activated autoreactive T cells which are reactive with a citrullinated antigen bound to an MHC class II shared epitope positive cell, said test kit comprising one or more citrullinated peptide antigens as disclosed herein. In aspects the peptide antigens may be selected from any one of SEQ ID NO. 1-37, SEQ ID NO. 38-39, SEQ ID NO. 40-48 and SEQ ID NO. 49-60.

The invention additionally provides citrullinated peptide antigens, optionally in association with a carrier, for use in a method of treating or preventing RA or MS, by desensitizing said T cells which recognize the citrullinated peptide antigens.

According to still a further aspect of the present invention is a method for treating a subject suffering from RA evoked by the binding of a citrullinated peptide to MHC class II molecules with the shared epitope leading to a T cell response, said method comprising;

administering a T cell tolerance inducing amount of a composition comprising a citrullinated peptide comprising an amino acid sequence selected from the group consisting of: SAVRACitSSVPGVR (SEQ ID NO. 1); FSMCitIVCLV (SEQ ID NO. 2); VVECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); and VETCitDGQVI (SEQ ID NO. 37), together with a pharmaceutically acceptable carrier.

According to still a further aspect of the present invention is a method for treating a subject suffering from MS evoked by the binding of a citrullinated peptide to MHC class II molecules with the shared epitope leading to a T cell response, said method comprising;
  administering a T cell tolerance inducing amount of a composition comprising a citrullinated peptide of FLPCitHRDTG (SEQ ID NO. 40), VTPCitTPPPS (SEQ ID NO. 41); YGGCitASKYK (SEQ ID NO. 42), LGGCitDSRSG (SEQ ID NO. 43), MERCitRITSA (SEQ ID NO. 44), LPTCitVDFSL (SEQ ID NO. 45), LNDCitFASYI (SEQ ID NO. 46), LRLCitLDQLT (SEQ ID NO. 47), LQICitETSLD (SEQ ID NO. 48) and VEMCitDGEVI (SEQ ID NO. 49).

According to still another aspect of the present invention is a diagnostic method for the detection of citrullinated antigen MHC class II cell complexes, said method comprising;
  incubating an isolated sample of peripheral blood mononuclear cells from a subject with one or more citrullinated peptide antigens;
  detecting the formation of citrullinated peptide antigen MHC class II cell complexes, such detection indicating a likelihood of evoking a T cell response leading to RA or MS in said subject.

According to another aspect of the present invention is a method for preventing the activation of T cells by a citrullinated peptide MHC class II complex in a subject, said method comprising administering antibodies targeted to said complex.

According to another aspect of the present invention is a method for preventing the conversion of an arginine to citrulline in a potentially antigenic peptide and thus the formation of citrullinated peptide MHC class II complexes in a subject, said method comprising administering an antagonist or inhibitor of peptidylarginine deiminase to said subject. In aspects, PAD inhibition may be effected using methods of RNA interference.

According to yet another aspect of the present invention is a screening method to identify pharmaceutical compounds that may block the binding of a citrullinated peptide to a MHC class II molecule having the shared epitope, the method comprising;
  administering to a transgenic DR4-IE tg mouse a candidate pharmaceutical compound; and
  measuring T cell activity and/or measuring citrullinated peptide/MHC class II molecule complex formation, wherein decreased T cell activity and/or decreased complex formation indicates said candidate pharmaceutical compound affects the binding of said citrullinated peptide to the MHC class II molecule.

According to a further aspect of the present invention is a screening method to identify inhibitors of PAD, the method comprising;
  (a) providing a mixture of uncitrullinated peptide, PAD and inhibitor;
  (b) provide antigen presenting cells to (a); and
  (c) apply (b) to a T-cell line specific for a peptide-MHC complex, wherein PAD inhibition is characterized by a lack of T-cell reactivity.

According to another aspect of the present invention is a method of inducing rheumatoid arthritis in an animal to provide an animal model for the study of rheumatoid arthritis, comprising administering to said animal a rheumatoid arthritis inducing amount of a composition comprising a citrullinated peptide together with a pharmaceutically acceptable carrier. Administration may be done by injection.

According to another aspect of the present invention is a method of inducing multiple sclerosis in an animal to provide an animal model for the study of multiple sclerosis, comprising administering to said animal a multiple sclerosis inducing amount of a composition comprising a citrullinated peptide together with a pharmaceutically acceptable carrier. Administration may be done by injection. In aspects, the citrullinated peptide is citrullinated myelin basic protein (MBP) or glial fibrillary acidic protein (GFAP).

According to still another aspect of the present invention is a method to make a citrullinated peptide antigen capable of binding to an MHC class II molecule with a shared epitope, said method comprising:
  (a) adding peptidyl deiminase to an endogenous or exogenous solubilized protein that contains at least one arginine amino acid residue for a time sufficient to convert the arginine to citrulline; and
  (b) isolating the protein from (a).

According to still another aspect of the present invention is a method for treatment of autoimmune disorders where the autoimmune disorder is characterized by the binding and formation of a citrullinated peptide/MHC class II complex in a mammal, the method comprising blocking the expression of peptidylarginine deiminase (PAD) enzyme in said mammal, wherein such blocking decreases the generation of citrullinated peptides that evoke rheumatoid arthritis.

According to a further aspect of the present invention is a method for the treatment of rheumatoid arthritis in a mammal, the method comprising inhibiting the expression of peptidylarginine deiminase (PAD) in a mammal by administration of siRNA targetted to the PAD gene sequence.

According to yet a further aspect of the present invention is a method for the treatment of rheumatoid arthritis or multiple sclerosis in a mammal, the method comprising administering to said mammal an agent that blocks the function of PAD.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

BRIEF DESCRIPTION OF THE DRAWINGS

The present invention will become more fully understood from the detailed description given herein and from the accompanying drawings, which are given by way of illustration only and do not limit the intended scope of the invention.

In FIG. 1B HLA-DR restriction of the recall T cell response was determined by incubating draining lymph node cells in vitro without antigen (control), with 10 µg/ml of the immunizing antigen (P4D left panel, P4Cit right panel), or in the presence of immunizing antigen (10 µg/ml) and anti-DR antibody (DR). Results represent the average proliferative response±SD of 4 mice for each immunizing antigen. FIG. 1C shows the IFN-γ production in response to in vitro challenge with 10 µg/ml of the immunizing peptide (P4D, P4Cit, or P4R). Cytokine production was determined by ELISA and represents the average antigen specific IFN-γ production±SD of 4 mice for each peptide tested.

In FIG. 2A DR4-IE tg mice were immunized with the indicated peptides and 10 days later draining lymph node cells were challenged in vitro with the same peptide at various concentrations. Data represents the average proliferative response±SEM of 8 mice for each peptide tested. FIG. 2B shows the specificity and HLA-DR restriction of the T cell recall response from Vim R70Cit immunized mice (left panel) and Vim 65-77 immunized mice (right panel). Draining lymph node cells were challenged with the immunizing peptide, the immunizing peptide plus anti-DR antibody (DR), the unmodified vimentin peptide (65-77 in left panel), or the citrulline containing vimentin peptide (R70Cit in right panel). The concentration used for in vitro challenge was 10 µg/ml and the results represent the average stimulation index±SEM of 4 mice for each immunizing antigen. FIG. 2C shows IFN-γ production in response to an in vitro challenge with varying concentrations of the immunizing peptide (Vim R70Cit or Vim 65-77). Cytokine production was determined by ELISA and represents the average antigen specific IFN-γ production±SD of 4 mice for each peptide tested.

FIG. 4 shows how the enzyme peptidylarginine deiminase (PAD) converts the positively charged imino group of arginine to the polar uncharged carbonyl group of citrulline.

FIG. 6A shows the clinical appearance of arthritis of hind paws from an unimmunized mouse, 6B is an arthritic mouse immunized with human fibrinogen and 6C is an arthritic mouse immunized with citrullinated human fibrinogen. FIGS. 6D and 6E are H&E sections showing the pathology of the tibiotalar joint of the mice from 6C while 6F is the section from the mouse shown in 6B.

DETAILED DESCRIPTION OF THE PREFERRED EMBODIMENTS

Figure 1A:
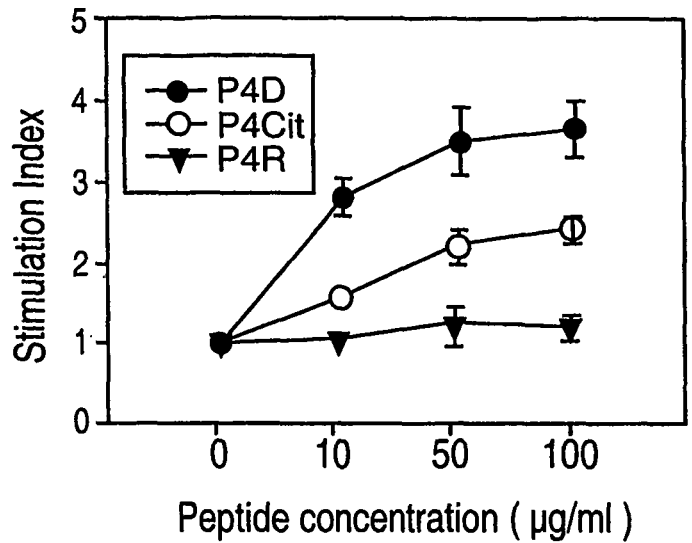
FIGS. 1A, 1B and 1C are graphs representing an analysis of the T cell immune response in DR4-IE tg mice to peptides containing arginine (P4R), citrulline (P4Cit), or aspartic acid (P4D) at the position that interacts with the P4 pocket formed by the shared epitope. In graph 1A DR4-IE tg mice were immunized with the indicated peptides and 10 days later draining lymph node cells were challenged in vitro with the same peptide at various concentrations. Data represents the average proliferative response±SEM of 8 mice for each peptide tested.

The Applicant has developed and identified novel citrullinated antigenic peptides that specifically bind to MHC class II molecules with the shared epitope leading to the activation of T cells and consequently, the development of rheumatoid arthritis. The conversion of arginine to citrulline at a peptide side-chain position that interacts with the shared epitope (P4) significantly increases peptide-MHC affinity and leads to the activation of CD4+ T cells. Such T cell activation further leads to synovial inflammation and the development of rheumatoid arthritis. It is understood by those of skill in the art that the citrullinated peptide antigens of the invention may be involved in a variety of autoimmune disorders characterized by the binding and formation of a citrullinated peptide/MHC class II with the shared epitope complex resulting in the activation of T cells and a development of an inflammatory response. Therefore, the present invention has several applications for autoimmune disorders involving such an etiology.

Using HLA-DRB1*0401 transgenic (DR4-IE tg) mice, the Applicant has demonstrated increased T cell responses to citrulline containing peptides. Using a model to predict MHC-peptide affinity, candidate T cell epitopes were developed and selected for study, including those from vimentin, fibrinogen and proteoglycan aggrecan. In the case of proteoglycan aggrecan, this protein normally contains a negatively charged aspartic acid (D) that interacts with the P4 shared epitope. Fibrinogen and vimentin peptides were chosen based on the property of binding to DRB1*0401 in a register that would position either arginine or citrulline at the positively charged P4 anchoring pocket (shared epitope). The conversion of arginine to citrulline, a process which replaces the charged imino side-chain group with an uncharged carbonyl, dramatically increased the affinity of the peptide for DRB1*0401. Furthermore, this post-translational modification was necessary to elicit a CD4+ T cell response to these peptides in DR4-IE tg mice. Peptide affinity for a number of HLA alleles was assessed and showed that only MHC class II molecules with the shared epitope had an increased affinity for the citrulline containing peptide. These studies, which identify a novel peptide-MHC interaction, help to explain the molecular basis of disease associated HLA alleles in RA and now provide for new diagnostic and therapeutic strategies for rheumatoid arthritis. The third hyper-variable region of MHC class II molecules associated with RA contains the amino acid sequence Q/R, K/R, R, A, A, spanning positions 70-74 of the DRβ chain. This shared epitope region forms one of the major peptide anchoring pockets known as P4, and is positively charged due to the K or R at position 71 which can make direct contact with side chain residues from the antigenic peptide (Dessen A, Lawrence C M, Cupo S, Zaller D M, Wiley DC. 1997. X-ray crystal structure of HLA-DR4 (DRA*0101, DRB1*0401) complexed with a peptide from human collagen II. *Immunity*. 7:473; Stern L J, Brown J H, Jardetzky T S, Gorga J C, Urban R G, Strominger J L, Wiley D C. 1994. Crystal structure of the human class II MHC protein HLA-DR1 complexed with an influenza virus peptide. *Nature*. 368:215). Previous studies on peptide-MHC affinity have shown that K or R at position 71 dictates the properties of the amino acid that can interact at this P4 pocket (Hammer J., Gallazzi F., Bono E., Karr R. W., Guenot J., Valsasnini P., Nagy Z. A., Sinigaglia F. 1995. Peptide binding specificity of HLA-DR4 molecules: correlation with rheumatoid arthritis association. J. Exp. Med. 181:1847). In general, MHC with the shared epitope have a high affinity for negatively charged or uncharged polar amino acids, while positively charged amino acids (i.e. arginine) inhibit peptide binding (Hammer J, Bono E, Gallazzi F, Belunis C, Nagy Z, Sinigaglia F. 1994. Precise prediction of major histocompatibility complex class II-peptide interaction based on peptide side chain scanning. *J. Exp. Med.* 180: 2353; Hammer J., Gallazzi F., Bono E., Karr R. W., Guenot J., Valsasnini P., Nagy Z. A., Sinigaglia F. 1995. Peptide binding specificity of HLA-DR4 molecules: correlation with rheumatoid arthritis association. *J. Exp. Med.* 181:1847). The Applicant has demonstrated that deimination via action of the enzyme peptidyl arginine deiminase (PAD) (FIG. 4) positively charged arginine is converted to polar but uncharged citrulline (a post-translational modification) which increases the affinity to the shared epitope P4 pocket. Since amino acid interactions at MHC anchoring pockets are not only dependent on the charge of the residue but also the size, the Applicant also confirmed that the P4 pocket formed by the shared epitope was large enough to accommodate the side chain of citrulline. This was verified by molecular modeling using the crystal structure of DRB1*0401 and DRB1*0101 (data not shown). Based on the charge properties of the P4 shared epitope and the size of this pocket, peptide bound citrulline was predicted to interact favourably at the P4 anchoring pocket of HLA*0401 and HLA*0101.

Figure 1B:
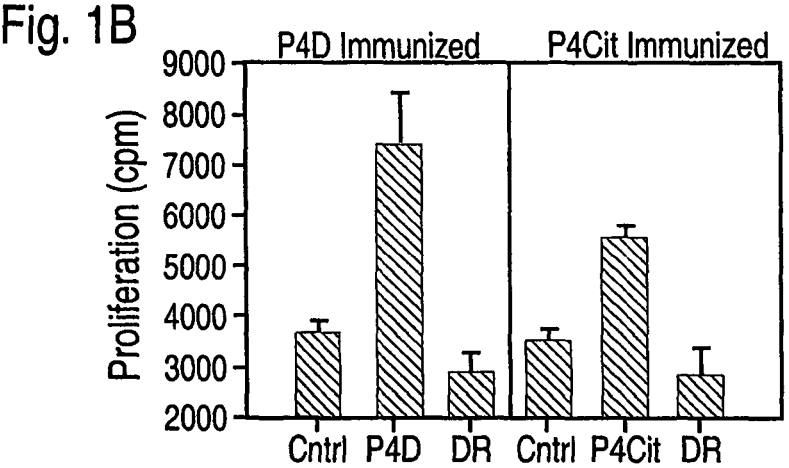
Figure 1C:
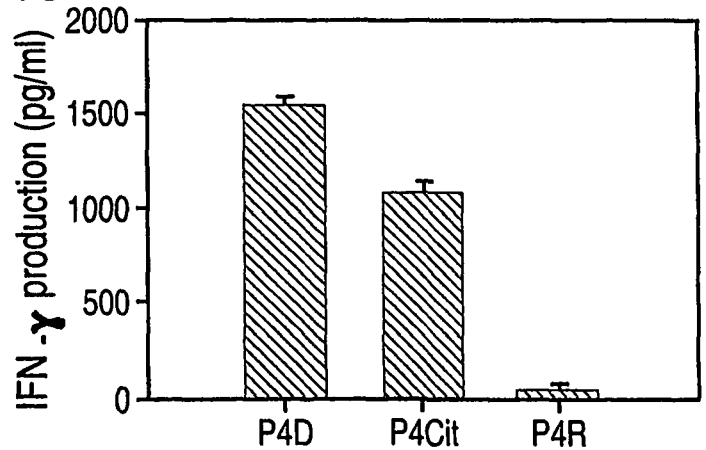
Figure 2A:
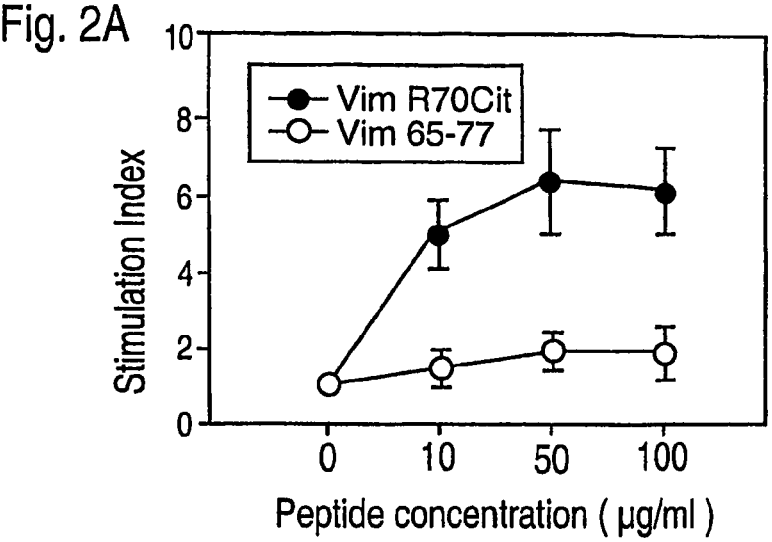
FIGS. 2A, 2B and 2C are graphs showing an analysis of the T cell immune response in DR4-IE tg mice to the unmodified vimentin peptide (Vim 65-77) or the citrulline containing vimentin peptide (Vim R70Cit).
Figure 2B:
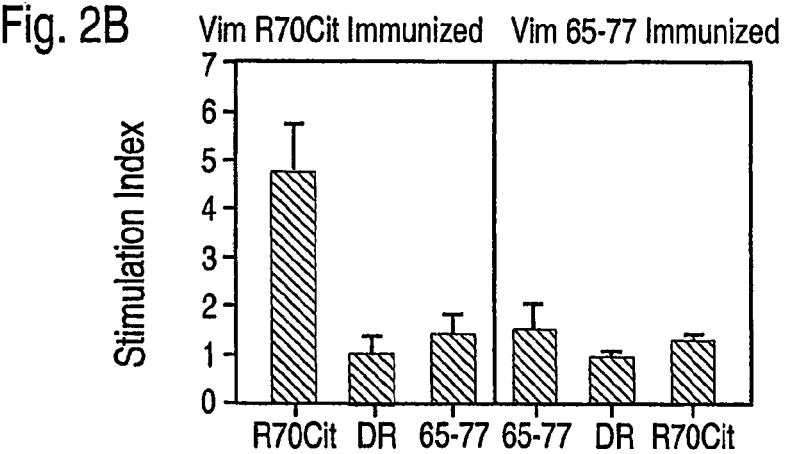
Figure 2C:
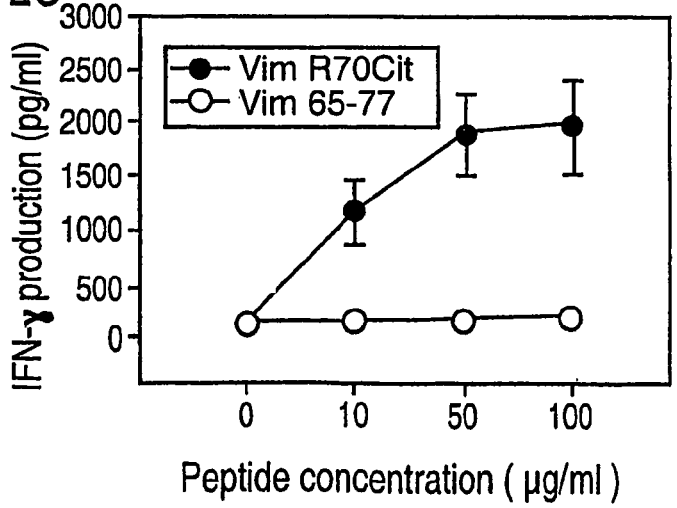

A peptide sequence was developed and chosen that was demonstrated by the Applicant to activate CD4+ T cells from DR4-IE tg mice. This peptide (from the cartilage proteoglycan aggrecan) normally contains a negatively charged aspartic acid (D) that interacts with the P4 shared epitope (P4D). Two additional peptides were synthesized based on this sequence: one had aspartic acid substituted by arginine (P4R); and the other had citrulline substituted at this position (P4Cit). DR4-IE tg mice were then immunized with these peptides and T cell responses were assessed 10 days later. The peptide P4D induced a strong proliferative response that was accompanied by IFN-γ production (FIGS. 1A and 1B). The peptide containing the arginine substitution (P4R), however, did not induce T cell proliferation or cytokine production in these mice. In contrast to an absent response for P4R, P4Cit induced T cell proliferation and IFN-γ production. To confirm that P4Cit was activating T cells through peptide-MHC presentation, anti-DR antibody was used to inhibit TCR interaction with the peptide-MHC complex (FIG. 1B). This treatment inhibited the proliferative response to P4Cit and P4D. Potential T cell epitopes from a protein target of anti-citrulline antibodies in RA patients were identified. Vimentin was selected since autoantibodies to this protein are frequently found in patients expressing the shared epitope (Goldbach-Mansky R, Lee J, McCoy A, Hoxworth J, Yarboro C, Smolen J S, Steiner G, Rosen A, Zhang C, Menard H A, Zhou Z J, Palosuo T, Van Venrooij W J, Wilder R L, Klippel J H, Schumacher H R Jr, El-Gabalawy H S. 2000. Rheumatoid arthritis associated autoantibodies in patients with synovitis of recent onset. *Arthritis Res.* 2:236). A candidate T cell epitope from human vimentin was identified using a predictive model for peptide-MHC affinity (Hammer J, Bono E, Gallazzi F, Belunis C, Nagy Z, Sinigaglia F. 1994. Precise prediction of major histocompatibility complex class II-peptide interaction based on peptide side chain scanning. *J. Exp. Med.* 180:2353). This peptide was selected based on the properties of having favourable interactions with the MHC anchoring pockets P1, P6, and P9, and having an arginine at the P4 shared epitope. Two peptides were synthesized, one containing the unmodified peptide Vimentin 65-77 and the other Vimentin R70Cit, in which arginine was substituted by citrulline. T cell responses to these peptides were then characterized using DR4-IE tg mice. As expected, the unmodified peptide Vim 65-77 did not induce T cell activation, however, Vim R70Cit stimulated a strong proliferative response that was accompanied by IFN-γ production (FIGS. 2A and 2C). T cell responses to Vim R70Cit could also be inhibited using anti-DR antibodies, confirming the MHC class II restricted immune response (FIG. 2B). It was also demonstrated that T cells primed by Vim R70Cit could not be activated by the unmodified peptide, further supporting that Vim 65-77 does not interact productively with the DR4 binding groove (FIG. 2B).

Figure 3:
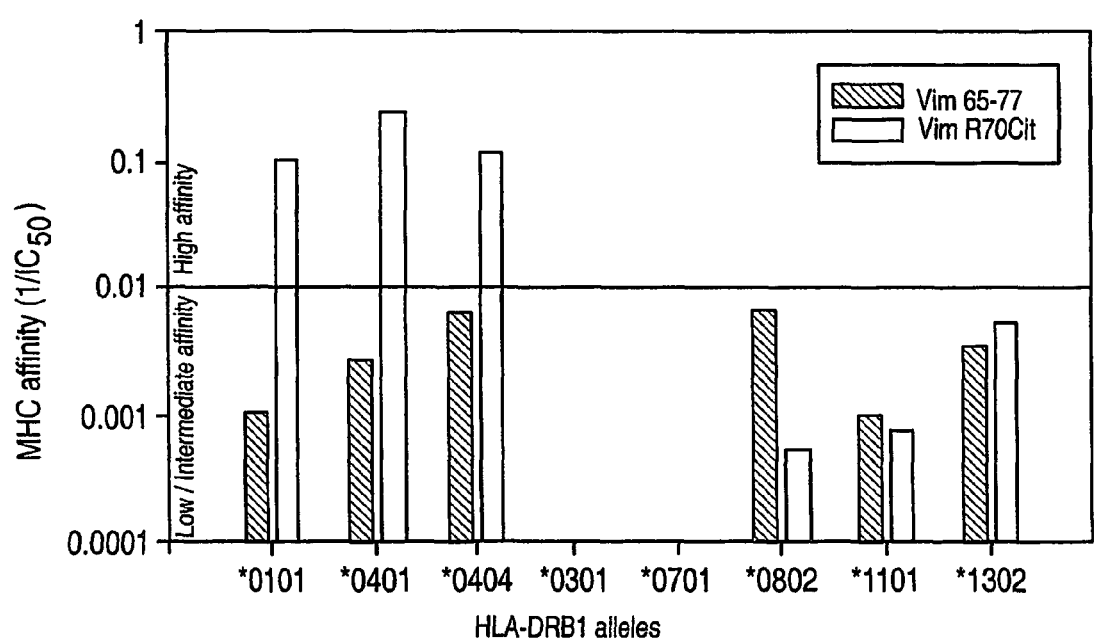
FIG. 3 is a graph showing the relative affinities of Vim 65-77 and Vim R70Cit for purified MHC class II molecules. Binding affinities to shared epitope positive (*0101, 0401, *0404) and negative alleles (*0301, *0701, *0802, *1101, *1302) were determined as described in the Examples described herein. Peptides with $IC_{50}$ values less than 100 nM are considered to be high affinity binders.

To confirm that the conversion of arginine to citrulline could increase peptide affinity for MHC class II molecules that contained the shared epitope, peptide competition assays were conducted to determine the relative affinity of Vim 65-77 and Vim R70Cit for purified MHC that were either shared epitope positive (DRB1*0101, *0401, *0404) or shared epitope negative (DRB1*0301, *0701, *0802, *1101, *1302). While Vim 65-77 had a low to intermediate affinity for all MHC tested, Vim R70Cit bound *0101, *0401, and *0404 with a strikingly high affinity (FIG. 3). Compared to the unmodified peptide, the citrulline containing peptide bound with 100 fold, 90 fold, and 20 fold higher affinity to *0101, *0401, and *0404 respectively. Most importantly, the conversion of arginine to citrulline did not increase peptide affinity for any shared epitope negative MHC tested.

Figure 5A:
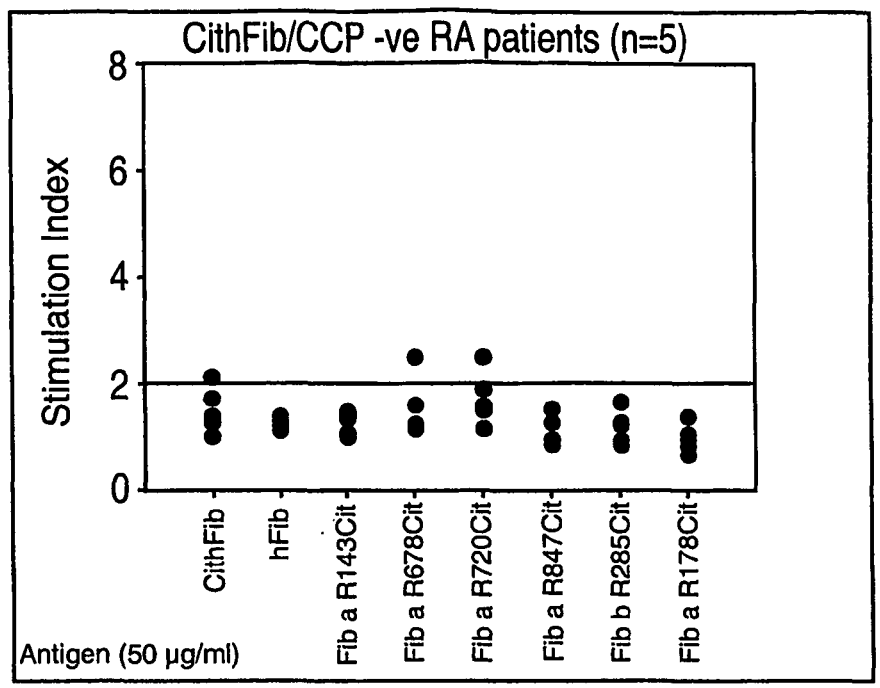
FIGS. 5A-5C show the T-cell proliferative response to citrullinated fibrinogen peptides in (5A) RA patients that are negative for anti-citrulline antibodies; 5B the RA patients that are positive for anti-citrulline antibodies; 5C the non-RA patients with other rheumatic diseases. The T-cell proliferation against the citrullinated fibrinogen peptides was only seen in RA patients and was more common in those patients that had anti-citrulline antibodies. The peripheral blood mononuclear cells were isolated from RA and non-RA donors by Ficoll-Hypaque centrifugation and cultured as described in example 4 for T cell cultures. The peptides used in these experiments are as follows: Fib a R143Cit=VLKCitKVIEK (SEQ ID NO. 6); Fib a R673Cit=IQQCitMDGSL (SEQ ID NO. 11); Fib a R720Cit=LTQCitGSVLR (SEQ ID NO. 12); Fib a R847Cit=VSFCitGADYS (SEQ ID NO. 15); Fib b R285Cit=IQNCitQDGSV (SEQ ID NO. 20); Fib a R178Cit=IKICitSCRGS (SEQ ID NO. 7).
Figure 5B:
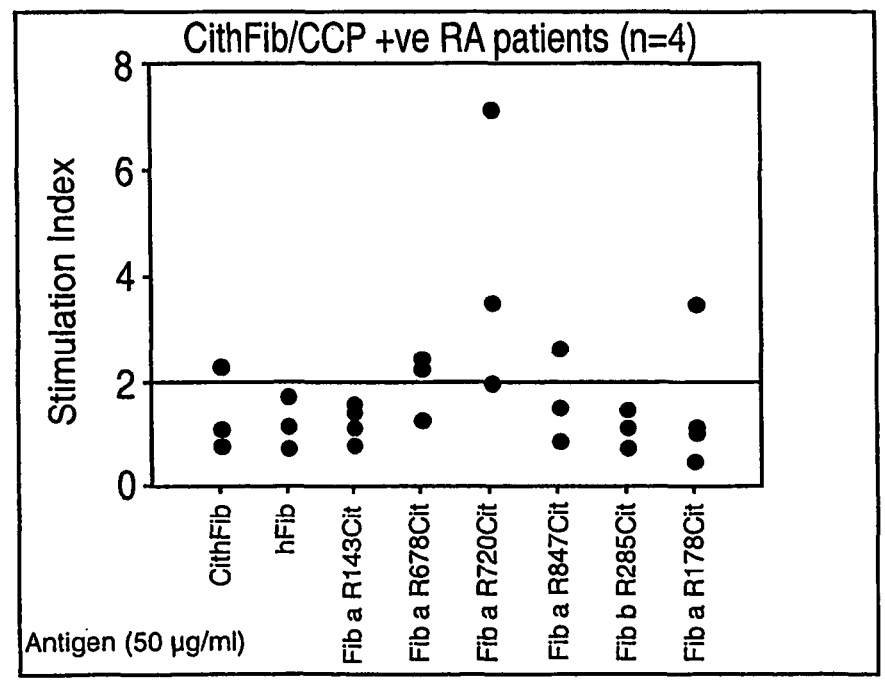
Figure 5C:
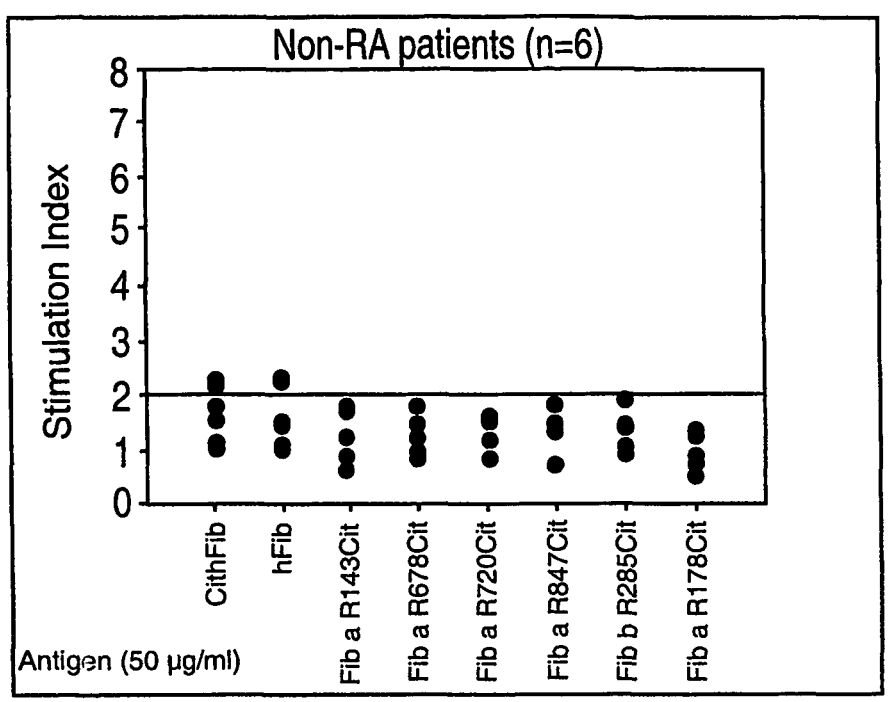
Figure 6A:
FIGS. 6A-F are photographs showing the clinical and pathological features of arthritis induced by citrullinated fibrinogen in SE tg mice.
Figure 6B:
Figure 6C:
Figure 6E:
Figure 6D:
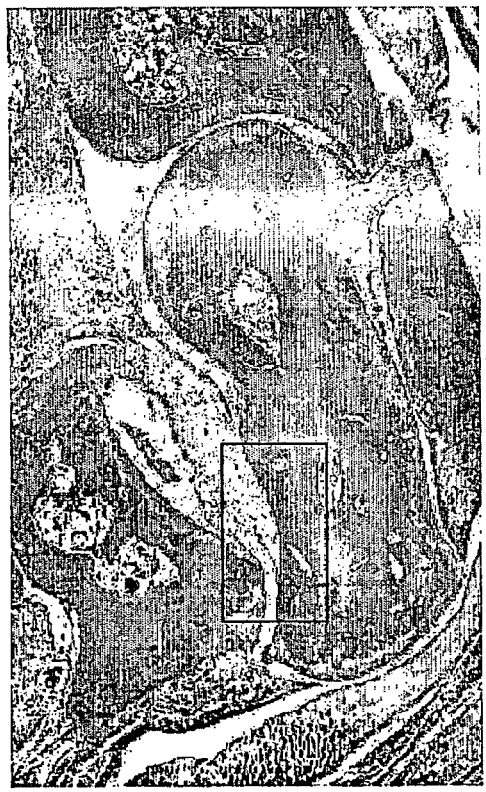
Figure 6F:

The Applicant's results indicated that the differential binding properties of DRB1 alleles to either arginine or citrulline at P4 explain how MHC class II molecules are disease associated, non-associated, or protective. First, the conversion of peptide bound arginine to citrulline causes a 100-fold increase in affinity for MHC with the shared epitope. This could result in a higher density of peptide-MHC complexes on antigen presenting cells which may exceed the "biochemical margin of safety" necessary for T cell activation (Peterson D A, DiPaolo R J, Kanagawa O, Unanue E R. 1999. Cutting edge: negative selection of immature thymocytes by a few peptide-MHC complexes: differential sensitivity of immature and mature T cells. *J. Immunol.* 162:3117; DiPaolo R J, Unanue E R. 2001. The level of peptide-MHC complex determines the susceptibility to autoimmune diabetes: studies in HEL transgenic mice. *Eur. J. Immunol.* 31:3453; Yagi J, Janeway C A Jr. 1990. Ligand thresholds at different stages of T cell development. *Int. Immunol.* 2:83). Second, non-associated MHC class II molecules (e.g. *0301) may contain P4 pockets that lack the proper size or charge to productively accommodate the large polar side-chains of arginine or citrulline, and would therefore be unable to bind and present peptides regardless of the state of modification (Ghosh P, Amaya M, Mellins E, Wiley D C. 1995. The structure of an intermediate in class II MHC maturation: CLIP bound to HLA-DR3. *Nature.* 378:457). Finally, disease protective MHC may interact productively with both arginine and citrulline at P4 resulting in peptide-MHC ligands that may induce negative selection, lead to the production of CD4+CD25+ regulatory T cells (Jordan M S, Boesteanu A, Reed A J, Petrone A L, Holenbeck A E, Lerman M A, Naji A, Caton A J. 2001. Thymic selection of CD4+CD25+ regulatory T cells induced by an agonist self-peptide. *Nat. Immunol.* 2:301), or simply remain within the "biochemical margin of safety" (Peterson D A, DiPaolo R J, Kanagawa O, Unanue E R. 1999. Cutting edge: negative selection of immature thymocytes by a few peptide-MHC complexes: differential sensitivity of immature and mature T cells. *J. Immunol.* 162:3117). The Applicant has also demonstrated that in RA patients positive for anti-citrulline antibodies, an increased T cell proliferative response was still seen to citrullinated fibrinogen peptides (FIG. 5A, B, C).

Taken together, the present invention demonstrates a set of peptides that in aspects are based on mammalian fibrinogen and vimentin amino acid sequences and in other aspects based on artificial citrullinated peptide sequences. The term "peptide" as used herein is defined as a chain of amino acid residues, usually having a defined sequence. As used herein the term peptide is mutually inclusive of the terms "peptides" and "proteins". In an aspect, the fibrinogen and vimentin sequences are human amino acid sequences. However, it is understood by one of skill in the art that the fibrinogen or vimentin sequences may be from any mammalian species such as but not limited to human, cow, pig, mouse and rat.

The invention also encompasses both the full length fibrinogen and vimentin amino acid sequences having at least one of the arginine amino acids converted to a citrulline, or fragments thereof. The limitation being that any fragment of any desired length has at least one citrulline that binds with high affinity to any MHC class II molecule with the shared epitope. One of skill in the art would understand that several additional sequences within vimentin and the alpha and beta chains of fibrinogen are predicted to bind the HLA-DR molecules in a register that would position arginine or citrulline at P4 and thus are embodied in the present invention. Furthermore, the invention encompasses any peptide that is demonstrated to be a potential target of anti-citrulline antibodies in RA patients. This suggests that a number of unique pathogenic peptides give rise to activated T cell with a heterogeneous array of specificities.

In one aspect of the invention any endogeneous or exogenous protein or peptide that is susceptible to modification by peptidylarginine deiminase (PAD), and further has the property of binding MHC Class II molecules with the shared epitope, is embodied by the present invention. Such proteins and peptides in one aspect can be found present in the joints and may include, but are not limited to, vimentin and fibrinogen.

The citrullinated peptides of the invention bind with high affinity to a MHC class II molecule having the shared epitope. It is understood by one of skill in the art, that "high affinity" as used herein refers to the capability of the citrullinated peptides to bind with higher or increased affinity to the MHC class II molecule having the shared epitope compared with a non-citrullinated peptide, such as a peptide having an arginine amino acid rather than citrulline. It is further understood that such binding affinity can be readily established for example in vitro using a peptide binding assay in which a sample peptide is used to displace a standard peptide (see example section).

In one embodiment, proteins of the present invention may include but are not limited to citrullinated peptides comprising at least one of the amino acid sequences selected from the group consisting of: SAVRACitSSVPGVR (SEQ ID NO. 1); FSMCitIVCLV (SEQ ID NO. 2); WECitHQSAC (SEQ ID NO. 3); FTNCitINKLK (SEQ ID NO. 4); LRSCitIEVLK (SEQ ID NO. 5); VLKCitKVIEK (SEQ ID NO. 6); IKICitSCRGS (SEQ ID NO. 7); LPSCitDRQHL (SEQ ID NO. 8); FRHCitHPDEA (SEQ ID NO. 9); FPSCitGKSSS (SEQ ID NO. 10); IQQCitMDGSL (SEQ ID NO. 11); LTQCitGSVLR (SEQ ID NO. 12); YHFCitVGSEA (SEQ ID NO. 13); YDPCitNNSPY (SEQ ID NO. 14); VSFCitGADYS (SEQ ID NO. 15); YSLCitAVRMK (SEQ ID NO. 16); MKICitPLVTQ (SEQ ID NO. 17); YRACitPAKAA (SEQ ID NO. 18); WQKCitQKQVK (SEQ ID NO. 19); IQNCitQDGSV (SEQ ID NO. 20); WYNCitCHAAN (SEQ ID NO. 21); YSMCitKMSMK (SEQ ID NO. 22); MKICitPFFPQ (SEQ ID NO. 23); LHPCitNLILY (SEQ ID NO. 24); VATCitDNCCI (SEQ ID NO. 25); LDECitFGSYC (SEQ ID NO. 26); LKSCitIMLEE (SEQ ID NO. 27); FQKCitLDGSV (SEQ ID NO. 28); YALCitVELED (SEQ ID NO. 29); WNGCitTSTA (SEQ ID NO. 30); WKTCitWYSMK (SEQ ID NO. 31); YATCitSSAVR (SEQ ID NO. 32); VRLCitSSVPG (SEQ ID NO. 33); LNDCitFANYI (SEQ ID NO. 34); MLQCitEEAEN (SEQ ID NO. 35); LNLCitETNLD (SEQ ID NO. 36); and VETCitDGQVI (SEQ ID NO. 37).

Certain of these peptide sequences may contain additional arginines that may be converted to citrulline via the action of the enzyme peptidylarginine deiminase. For example, the citrullinated peptides of the invention may have a formula as follows: Cit-Cit-X-Cit-G-Cit-Cit-Z-Cit-Cit-B-Cit-Cit (SEQ ID NO. 38), wherein X is selected from Y, F, W, I, L, M and V; Z is selected from A, D, I, N, P, S, T, V; and B is selected from A, G, H, Q, S, T and V. The amino acid indicated as "X" is required for P1 anchoring amino acids for MHC class II molecules with the shared epitope. The glycine present at position number 5 helps to reduce the torsion on the peptide backbone in order to allow for citrulline to be placed at amino acid position numbers 4, 6 and 7. The amino acid at position 6 is the P4 shared epitope pocket. The amino acids selected at position number 8 are non-inhibitory at the P6 anchoring pocket for MHC class II molecules with the shared epitope. The amino acids selected at position number 11 are non-inhibitory at the P9 anchoring pocket for MHC class II molecules with the shared epitope. In aspects of the invention the peptide comprises Cit-Cit-Y-Cit-G-Cit-Cit-S-Cit-Cit-S-Cit-Cit (SEQ ID NO. 39). In further aspects of the invention, positively charged amino acids and/or negatively charged amino acids can be added at the carboxy terminus and/or the amino terminus of the peptide to increase peptide binding. Furthermore, this peptide may have cysteines added to one or both ends of the peptide to circularize the peptide by the formation of disulfide bond formation.

The peptides of the formula: Cit-Cit-X-Cit-G-Cit-Cit-Z-Cit-Cit-B-Cit-Cit (SEQ ID NO. 38), wherein X is selected from Y, F, W, I, L, M and V; Z is selected from A, D, I, N, P, S, T, V; and B is selected from A, G, H, Q, S, T and V have been demonstrated to generate anti-citrulline antibodies in DR4 tg mice. Furthermore, these peptides have also been demonstrated to react with autoantibodies in human sera of RA patients. As such these peptides can be used in methods and kits for the diagnosis of RA in subjects.

As the Applicant has demonstrated that autoimmune diseases involve citrullinated peptide antigens evoke a T cell response in those subjects carrying the MHC class II shared epitope, citrullinated peptides evoking T cell responses in multiple sclerosis (MS) are also encompassed in the present invention for those MS subjects carrying the MHC class II epitope. Such citrullinated peptides may include for example citrullinated myelin basic protein (MBP) and citrullinated glial fibriallry acid protein (GFAP). Citrullinated MBP and GFAP peptides useful in the diagnosis of MS and the target of therapeutic methods may comprise amino acid sequences selected from the group consisting of FLPCitHRDTG (SEQ ID NO. 40), VTPCitTPPPS (SEQ ID NO. 41); YGGCitASKYK (SEQ ID NO. 42), LGGCitDSRSG (SEQ ID NO. 43), MERCitRITSA (SEQ ID NO. 44), LPTCitVDFSL (SEQ ID NO. 45), LNDCitFASYI (SEQ ID NO. 46), LRLCitLDQLT (SEQ ID NO. 47), LQICitETSLD (SEQ ID NO. 48) and VEMCitDGEVI (SEQ ID NO. 49).

Furthermore, citrullinated peptides of the invention may further encompass a peptide that is citrullinated in neutrophils and as such, may be used in the diagnostically or in the treatment of rheumatoid arthritis, said peptides being selected from the group consisting of: nucleophosmin/B23, Histone H2A, Histone H4 and Histone H3 wherein said peptide contains one or more citrulline residues. These proteins have been demonstrated to be citrullinated in granulocytes (Hagiwara T. et al., Biochem & Biophy Res Comm. (2000) 290, 979-983). Neutrophils are present in inflammatory joints of rheumatoid arthritis patients. The peptides that may be citrullinated are selected from the group consisting of: LSLRTVSLG (SEQ ID NO. 50, nucleophosmin/B23); WLRLKCGS (SEQ ID NO. 51, nucleophosmin/B23); MSGRGKQGG (SEQ ID NO. 52, histone H2A); YSERVGAGA (SEQ ID NO. 53, Histone H2A); IIPRHLQLA (SEQ ID NO. 54, histone H2A); LAIRNDEEL (SEQ ID NO. 55, histone H2A); LLGRVTIAQ (SEQ ID NO. 56, histone H2A); MSGRGKGGK (SEQ ID NO. 57, histone H4); LARRGGVKR (SEQ ID NO. 58, histone H4); VALREIRRY (SEQ ID NO. 59, histone H3); LLIRKLPFQ (SEQ ID NO. 60, histone H3) and LARRIRGER (SEQ ID NO. 61, histone H3), wherein said "R" arginine residue may be converted to citrulline by the action of PAD. Such peptides may be used in various assays such as to measure T cell reactivity as a diagnostic indication of rheumatoid arthritis.

The peptides of the invention may be of about at least 9 amino acids in length and about 9 to about 55 amino acids in length and include any ranges of length therein (i.e 9-50, 9-45, 9-40, 9-35, 9-30, 9-25, 9-20, 9-15, etc.) as is understood by one of skill in the art. Peptides of over about 55 amino acids in length are also encompassed by the present invention. The length of peptide being only restricted by its binding capability to a MHC Class II molecule having the shared epitope. The peptides of the invention may also include dimers and trimers of the peptides as well as additional stabilizing flanking sequences as is understood by those of skill in the art and described for example in U.S. Pat. No. 5,824,315 and U.S. Pat. No. 6,184,204 (the disclosures of which are incorporated herein by reference in their entirety). A multimer according to the invention can either be a homomer, consisting of a multitude of the same peptide, or a heteromer consisting of different peptides. As stated, the amino acid sequences of the peptides according to the invention can be flanked by random amino acid sequences. Preferred are flanking sequences that have a stabilizing effect on the peptides, thus increasing their biological availability. In addition, other peptidomimetics are also useful in the peptides of the present invention. For a general review see A. F. Spatola, in Chemistry and Biochemistry of Amino Acids, Peptides and Proteins, B. Weinstein, eds., Marcel Dekker, New York, p. 267 (1983). The peptides of the invention also encompass peptides that have been modified by, for example, phosphorylation, glycosylation or lipidation. Furthermore, the polypeptides of the present invention may also encompass "functionally equivalent variants" or "analogues" of the peptides. As such, this would include but not be limited to peptides and polypeptides with partial sequence homology, peptides having one or more specific conservative and/or non-conservative amino acid changes and peptide conjugates which do not alter the biological or structural properties of the peptide (i.e. the ability to bind to an MHC class II molecule having the shared epitope).

In terms of "functional analogues", it is well understood by those skilled in the art, that inherent in the definition of a biologically functional peptide analogue is the concept that there is a limit to the number of changes that may be made within a defined portion of the molecule and still result in a molecule with an acceptable level of equivalent biological activity, which, in this case, would include the ability to bind to an MHC class II molecule having a shared epitope. A plurality of distinct peptides/proteins with different substitutions may easily be made and used in accordance with the invention. It is also understood that certain residues are particularly important to the biological or structural properties of a protein or peptide such as residues in the receptor recognition region, such residues of which may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the peptide. Examples of such conservative changes are well-known to the skilled artisan and are within the scope of the present invention. Conservative substitution also includes the use of a chemically derivatized residue in place of a non-derivatized residue provided that the resulting peptide is a biologically functional equivalent to the peptides of the invention. Therefore, the citrullinated peptides of the present invention encompass a peptide having an amino acid sequence that differs from SEQ ID Nos. 1-39 by one or more conservative amino acid substitutions. The citrullinated peptides of the invention also encompass a peptide having an amino acid sequence that differs from SEQ ID Nos. 1-39 by a single mutation, where the single mutation represents a single amino acid deletion, insertion or substitution.

The peptides of the present invention may be made by methods known to those of skill in the art most notably and preferably by chemical synthesis using techniques well known in the chemistry of proteins such as solid phase synthesis (Merrifield (1964) J. Am. Chem. Assoc. 65:2149; J. Amer. Chem. Soc. 85:2149 (1963); and Int. J. Peptide Protein Res. 35:161-214 (1990)) or synthesis in homogenous solution (Methods of Organic Chemistry, E. Wansch (Ed.) Vol. 15, pts. I and II, Thieme, Stuttgart (1987) to generate synthetic peptides. Citrulline is a post-translationally modified arginine that is created through the process of deimination which is catalyzed by the enzyme peptidylarginine deiminase (PAD) that removes a positive charge from arginine and makes the resulting citrulline polar in nature.

In one embodiment for citrullinated vimentin and fibrinogen, citrullinated peptides of the invention can be made from known commerically available sources of vimentin and fibrinogen. In this aspect, lyophilized vimentin or fibrinogen are reconstituted in an appropriate buffer to which the enzyme peptidylarginine deiminase is added. The solution is allowed to stand at an appropriate temperature for a time sufficient to cause modification of arginine residues to citrulline and thus create a citrullinated vimentin or fibrinogen protein. The citrullinated protein is then isolated by the removal of the enzyme using a high molecular weight membrane to separate the enzyme or other methods of chromatography. One of skill in the art will understand that the temperature of incubation, buffer condition and time of incubation may vary depending on the protein that is being deiminated (Christine Masson-Bessiere et al., 2001. The Major Synovial Targets of the Rheumatoid arthritis-Specific Antifilaggrin Autoantibodies Are Deiminated Forms of the α and β Chains of Fibrin 1 *The Journal of Immunology* 166: 4177-4184). In one aspect of the present invention, citrullinated fibrinogen was made by obtaining plasminogen-depleted human fibrinogen (Calbiochem, San Diego, Calif.) and incubating this protein at 0.86 mg/ml with rabbit skeletal muscle PAD (7 U/mg fibrinogen; Sigma) in 0.1 M Tris-HCl (pH 7.4), 10 mM $CaCl_2$, and 5 mM DTT for 2 hours at 50° C. for deimination of the protein. Similar approaches are encompassed for making and isolating myelin basic protein and glial fibrillary acid protein from suitable tissues and cells.

The citrullinated proteins of the invention may be further isolated and purified by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chomatography) or by precipitation (immunoprecipitation). Polyacrylamide gel electrophoresis can also be used to isolate the citrullinated proteins based on the molecular weight of the protein, charge properties and hydrophobicity. The purified citrullinated proteins can be used in further biochemical analyses to establish secondary and tertiary structure which may aid in the design of pharmaceuticals to interact with the protein, alter the protein charge configuration or charge interaction with other proteins or alter its function.

Alternatively, the citrullinated peptides of the invention may be made by the use of recombinant DNA techniques known to one skilled in the art. As citrulline is not encoded by any trinucleotide sequence, a nucleic acid sequence encoding for arginine may be used with the resultant protein sequence being modified using peptidylarginine deiminase (PAD) to convert the arginine to citrulline. It is further within the scope of the invention to use a nucleic acid sequence encoding for glutamine, an amino acid that resembles citrulline. In this manner, a naturally occurring sequence that contains arginine can be used in which the arginine is substituted with glutamine in order to resemble citrulline. Nucleic acid sequences which encode for the selected peptides of the invention may be incorporated in a known manner into appropriate expression vectors (i.e. recombinant expression vectors). Possible expression vectors include (but are not limited to) cosmids, plasmids, or modified viruses (e.g. replication defective retroviruses, adenoviruses and adeno-associated viruses, lentiviruses, herpes viruses, poxviruses), so long as the vector is compatible with the host cell used. The expression "vector is compatible with the host cell" is defined as contemplating that the expression vector(s) contain a nucleic acid molecule of the invention (hereinafter described) and attendant regulatory sequence(s) selected on the basis of the host cell(s) to be used for expression, said regulatory sequence(s) being operatively linked to the nucleic acid molecule. "Operatively linked" is intended to mean that the nucleic acid is linked to regulatory sequence(s) in a manner which allows expression of the nucleic acid. Suitable regulatory sequences may be derived from a variety of sources, including bacteria), fungal, or viral genes. (For example, see the regulatory sequences described in Goeddel, Gene Expression Technology: Methods in Enzymology 185, Academic Press, San Diego, Calif. (1990). Selection of appropriate regulatory sequence(s) is dependent on the host cell(s) chosen, and may be readily accomplished by one of ordinary skill in the art. Examples of such regulatory sequences include the following: a transcriptional promoter and enhancer, RNA polymerase binding sequence, or a ribosomal binding sequence (including a translation initiation signal). Depending on the host cell chosen and the expression vector employed, other additional sequences (such as an origin of replication, additional DNA restriction sites, enhancers, and sequences conferring inducibility of transcription) may be incorporated into the expression vector.

The peptides of the invention may also be produced recombinantly in association with a soluble MHC molecule using a variety of methods known to those of skill in the art (i.e. Hugues, S et al (2002) Generation and use of alternative multimers of peptide/MHC complexes. Journal of Immunological Methods. 268:83-91, the disclosure of which is incorporated herein in its entirety). Methods for making peptide/MHC class II soluble complexes are also provided in U.S. Pat. No. 5,869,279 (the disclosure of which is incorporated herein in its entirety).

It is further contemplated that the invention encompasses vectors which comprise nucleic acids coding for at least one member from the group consisting of cytokines, lymphokines and immunomodulatory molecules. Said nucleic acid sequences can be contiguous with sequences coding for the citrullinated peptide antigens of the invention, or encoded on distinct nucleic acids.

The peptides of the invention may be labelled with a label to facilitate their detection in a variety of assays as is understood by one of skill in the art. Such labels may include but are not limited to radioactive label and fluorescent label. The peptides of the invention may be provided with a carrier such as for example couple to bovine serum albumin (BSA) or keyhole limpet haemocyanin. The peptides may be covalently or non-covalently coupled to a solid carrier such as a microsphere of gold or polystyrene, a slide, chip or a wall of a microtitre plate. The peptide may be labelled directly or indirectly with a label selected from but not limited to biotin, fluorescin and an enzyme such as horseradish peroxidase.

An embodiment of the present invention further encompasses pharmaceutical compositions comprising one or more citrullinated peptides for administration to subjects in a biologically compatible form suitable for administration in vivo. The citrullinated peptides for use within a pharmaceutical composition may be made chemically or by recombinant DNA techniques. The administration of the citrullinated peptide antigens of the invention may act to desensitize (i.e. by inducing a state of systemic hyporesponsiveness or tolerance to said peptide or composition) the immune system in those patients having auto-responsive T cells and thus reduce the inflammatory response over time. The peptides of the invention may be provided within DNA expression vectors as described above that are formulated in a suitable pharmaceutical composition.

By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result of eliciting an immune response in a human. A therapeutically effective amount of a substance may vary according to factors such as the disease state/health, age, sex, and weight of the recipient, and the inherent ability of the particular polypeptide, nucleic acid coding therefor, or recombinant virus to elicit a desired immune response. Dosage regima may be adjusted to provide the optimum therapeutic response. For example, several divided doses may be administered daily or on at periodic intervals, and/or the dose may be proportionally reduced as indicated by the exigencies of the therapeutic situation. The amount of citrullinated peptide antigen for administration will depend on the route of administration, time of administration and varied in accordance with individual subject responses. Suitable administration routes are intramuscular injections, subcutaneous injections, intravenous injections or intraperitoneal injections, oral and intranasal administration. Oral and intranasal administration are preferred administration routes.

The compositions described herein can be prepared by per se known methods for the preparation of pharmaceutically acceptable compositions which can be administered to subjects, such that an effective quantity of the active substance (i.e. citrullinated peptide) is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water. Other carriers may be, for example MHC class II molecules. Soluble MHC class II molecules including monomers, dimers, trimers, tetramers, etc, as well as citrulline peptide/ MHC class II complexes can be made by methods disclosed in U.S. Pat. No. 5,869,270 (the disclosure of which is incorporated herein by reference).

Furthermore the pharmaceutical composition according to the invention may comprise one or more stabilizers such as, for example, carbohydrates including sorbitol, mannitol, starch, sucrose, dextrin and glucose, proteins such as albumin or casein, and buffers like alkaline phosphates.

The pharmaceutical composition of the invention may also comprise one or more adjuvants. As is well known to those of ordinary skill in the art, the ability of an immunogen to induce/elicit an immune response can be improved if, regardless of administration formulation (i.e. recombinant virus, nucleic acid, peptide), the immunogen is coadministered with an adjuvant. Adjuvants are described and discussed in "Vaccine Design—the Subunit and Adjuvant Approach" (edited by Powell and Newman, 'Plenum Press, New York, U.S.A., pp. 61-79 and 141-228 (1995)). Adjuvants typically enhance the immunogenicity of an immunogen but are not necessarily immunogenic in and of themselves. Adjuvants may act by retaining the immunogen locally near the site of administration to produce a depot effect facilitating a slow, sustained release of immunizing agent to cells of the immune system. Adjuvants can also attract cells of the, immune system to an immunogen depot and stimulate such cells to elicit immune responses. As such, embodiments of this invention encompass compositions further comprising adjuvants.

Desirable characteristics of ideal adjuvants include:
1) lack of toxicity:
2) ability to stimulate a long-lasting immune response;
3) simplicity of manufacture and stability in long-term storage;
4) ability to elicit both cellular and humoral responses to antigens administered by various routes, if required:
5) synergy with other adjuvants;
6) capability of selectively interacting with populations of antigen presenting cells (APC);
7) ability to specifically elicit appropriate Tr, TR1 or TH2 cell-specific immune responses; and
8) ability to selectively increase appropriate antibody isotype levels (for example, IgA) against antigens/ immunogens.

Suitable adjuvants include, amongst others, aluminium hydroxide, aluminium phosphate, amphigen, tocophenols, monophosphenyl lipid A, muramyl dlpeptide and saponins such as Quill A. Preferably, the adjuvants to be used in the tolerance therapy according to the invention are mucosal adjuvants such as the cholera toxine B-subunit or carbomers, which bind to the mucosal epithelium. The amount of adjuvant depending on the nature of the adjuvant itself as is understood by one of skill in the art.

It is further embodied within the present invention that the citrullinated peptides can be administered to a patient in combination with short double stranded RNA (less than 30 nucleotides in length) that mediate an RNA interference response against a desired gene. These target genes may be selected from one or more members of the group consisting of transcription factors, enzymes, cytokines, lymphokines and immunomodulatory molecules.

The peptides and compositions of the invention can be administered in the context of an MHC molecule. Thus, the polypeptides of this invention can be pulsed into antigen presenting cells which include, but are not limited to dendritic cells (DCs). More specifically, the citrullinated peptides may be administered to a patient via antigen pulsed dendritic cells (antigen presenting cells). In certain embodiments of the present invention use dendritic cells or progenitors thereof as antigen-presenting cells. These dendritic cells can be grown from the PBMCs (peripheral blood mononuclear cells) of a patient and treated ex vivo in order to alter their production of transcription factors, enzymes, cytokines, lymphokines, or immunomodulatory molecules, before administering to a patient. Dendritic cells are highly potent APCs (Banchereau and Steinman, Nature 392:245-251, 1998). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., Nature Med. 4:594-600, 1998). Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNF-α to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

The citrullinated peptides of the invention are arthritogenic and thus evoke an inflammatory response leading to RA. This is demonstrated in FIGS. 6A-E. As such, these peptides can be used to induce clinical arthritis in non-human mammalians in order to provide an animal model for which novel pharmaceuticals may be tested and identified effective for the treatment of RA. Any animal that is transgenic for a MHC class II molecule that contains the shared epitope may be used within the scope of the present invention. In one aspect of the invention, the administration of one or more of the citrullinated peptides of the invention may be provided to HLA-DRB1*401 transgenic mice (DR4-IE tg) leading to the development of arthritic signs and eventual disease patterns of arthritis, more particularly rheumatoid arthritis. These DR4-IE tg transgenic mice express a chimeric MHC class II molecule that is composed of the human antigen binding domains (α1 and β1) and mouse CD4 binding domains (α2 and β2). The chimeric DR4 presents peptides in an identical manner as full human DR4 and these mice do not express endogenous MHC class II molecules. Further, these mice contain the same complement of B and T cells as wild-type mice and thus these transgenic mice are ideal for testing the immune response of SE restricted T cells in vivo and thus for identifying pharmaceutical agents that may decrease or prevent a T cell response leading to inflammation. While DR4-IE tg mice were used, it is understood that any mouse strain that is transgenic for a MHC class II molecules that contains the shared epitope may be used as an animal model for the testing of pharmaceutical compounds in the present invention.

The citrullinated MBP and GFAP proteins of the invention may also be used to induce clinical multiple sclerosis in non-human mammals in order to provide an MS animal model for which novel pharmaceuticals may be tested and identified effective for the treatment of MS. Methods for making such animal models are as just described supra.

The transgenic mice may be injected one or more times subcutaneously, interdermally, intraperetonealy or intramuscularly with a citrullinated protein containing one or more peptides of the invention (as well as any adjuvants or other pharmaceutical excipients and allowed to develop arthritic signs. In one aspect, full length citrullinated vimentin or citrullinated fibrinogen are administered to the transgenic mice to induce the development of arthritis. Potential pharmaceutical agents may be coadministered with the peptides or later once an inflammatory reaction is established to treat arthritis and to study the effect of these pharmaceutical actives upon the arthritic development. Preferably mice are used as animal model for arthritis, especially rheumatoid arthritis.

In embodiments of the invention, the knowledge that the citrullinated peptides of the invention are arthritogenic and act via binding to MHC class II molecules with the shared epitope to evoke a T cell response leading to RA, now provides diagnostic and therapeutic methods for autoimmune disorders involving shared epitope binding of citrullinated antigens such as for RA and MS.

In one aspect, the present invention may be used to detect autoreactive T cells from patients with RA or those suspected or predisposed to developing RA. A number of methods may be used to detect either T cells specific for the citrullinated peptide-MHC complex or detecting the presence of the citrullinated peptide-MHC complex itself. For example, a T cell proliferation assay known to those of skill in the art may be used to detect T cell activation in a subject peripheral blood mononuclear blood (PBMC) sample. Such method is conducted by the incorporation of a radioisotope such as for example $^3$H-thymidine as a measure of T cell proliferation (see example section). Autoreactive T cell activity present in the PBMC can also be detected by measuring the cytokine release after activation by the citrullinated peptide-MHC class II complexes with cytokine-specific ELISA (i.e ELISPOT). Another detection method is the measurement of expression of activation markers by FACS analysis, for example of Il-2R. Furthermore, soluble MHC class II molecules may be linked to a fluorochrome or liposome with bound citrullinated peptide and used to detect T cells which possess T cell receptors that recognize these complexes.

In another embodiment, monoclonal antibodies that recognize any of the citrullinated peptides of the invention may also be made and used to detect the presence of the peptide as presented/bound to MHC class II molecules having a shared epitope on antigen presenting cells (APC). This provides a rapid and simple method of diagnosis of disease as well as the disposition to developing RA. In general, methods for the preparation of antibodies are well known. In order to prepare polyclonal antibodies that would recognize the peptides of the invention, fusion proteins containing defined portions or all of vimentin or fibrinogen proteins or any of their alternative transcripts can be synthesized in bacteria by expression of corresponding DNA sequences in a suitable cloning vehicle. The protein can then be purified, coupled to a carrier protein and mixed with Freund's adjuvant (to help stimulate the antigenic response by the rabbits) and injected into rabbits or other laboratory animals. Alternatively, protein can be isolated from cultured cells expressing the protein. Following booster injections at bi-weekly intervals, the rabbits or other laboratory animals are then bled and the sera isolated. The sera can be used directly or purified prior to use, by affinity chromatography. The sera can then be used to probe protein extracts run on a polyacrylamide gel to identify the vimentin or fibrinogen protein, alternative transcript or any mutant thereof. Alternatively, synthetic peptides (as discussed above) can be made to the antigenic portions of these proteins and used to innoculate the animals.

Methods to produce monoclonal antibodies which specifically recognize the peptides of the invention including but not limited to mammalian or other species of vimentin and fibrinogen proteins or portions thereof, are well known to those of skill in the art. In general, cells actively expressing the protein are cultured or isolated from tissues and the cell extracts isolated. The extracts or recombinant protein extracts, containing the vimentin or fibrinogen protein, are injected in Freund's adjuvant into mice. After being injected 9 times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable lines of clones is established which produce the antibody. The monoclonal antibody can then be purified by affinity chromatography using Protein A or Protein G Sepharose.

Methods for the preparation of the antibodies of the present invention are generally known in the art. For example, see Antibodies, A Laboratory Manual, Ed. Harlow & David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, R. et al. Monoclonal Antibodies, Hybridoma: A New Dimension In Biological Analyses Plenum Press, N.Y. (1980); and Campbell, A. "Monoclonal Antibody Technology," Laboratory Techniques In Biochemistry And Molecular Biology, Vol. 13, Burdon et al. (eds.), Elsevier, Amsterdam (1984). See also, U.S. Pat. Nos. 4,609,893; 4,713,325; 4,714,681; 4,716,111; 4,716,117; and 4,720,459 (the disclosures of which are incorporated herein in their entirety).

Antibodies can also be made directed to the peptide/MHC Class II complex. Methods to generate such antibodies to the peptide/MHC Class II complex are known and described (i.e. Baeten, D., Steenbakkers P G A., Rovers E., Veys E M., Rijnders A M W., Meijerink J., Keyser F De and Boots A. Localisation of MHC Class II/HC gp-39 complexes in synovia of rheumatoid arthritis patients using complex-specific monoclonal antibodies. Abstracts of the 23$^{rd}$ European Workshop for Rheumatology Research, Vol 5 Suppl 1, February 2003; Baeten D., Steenbakkers P., Boots A., Veys E M., and Keyser, Fde., The presentation of the immunodominant epitope of HC gp-39 in the context of the RA-associated HLA class II molecules is specific for RA synovium. Abstracts of the 23$^{rd}$ European Workshop for Rheumatology Research, Vol 5 Suppl 1, February 2003).

A diagnostic composition comprising one or more of the peptides according to the invention and a suitable detecting agent thus forms part of the invention. Depending on the type of detection, the detection agent can be a radioisotope, an enzyme, or antibodies specific for cell surface or activation markers.

Also within the scope of the invention are test kits which comprise one or more peptides according to the invention. These test kits are suitable for use in a diagnostic method according to the invention.

The peptides of the formula: Cit-Cit-X-Cit-G-Cit-Cit-Z-Cit-Cit-B-Cit-Cit (SEQ ID NO. 38), wherein X is selected from Y, F, W, I, L, M and V; Z is selected from A, D, I, N, P, S, T, V; and B is selected from A, G, H, Q, S, T and V are particularly useful in methods for the diagnosis of an autoimmune disorder. Such autoimmune disorders include but are not limited to rheumatoid arthritis. These peptides such as for example Cit-Cit-Y-Cit-G-Cit-Cit-S-Cit-Cit-S-Cit-Cit (SEQ ID NO. 39) can be used in a commercial test kit such as an ELISA kit to detect anti-citrulline antibodies in patients for the diagnosis of RA (ELISA Guidebook. Theory & Practice. Editor John R. Crowther, Author John R. Crowther, Pub. Humana Press 2000). Briefly, the peptide is covalently coupled or non-covalently bound to wells of a microtitre plate and diluted patient sera is added to each well and allowed to incubate for a period of time. After washing the plate an IgG conjugated to peroxidase is added to the wells and further incubated. After further washing bound antibodies are detected with a substrate such as tetramethyl benzidine. After some period of time the reaction is stopped and the OD readings of the plate at a certain wavelength (for example 450 nm) are read. Control samples are simultaneously treated in the same manner. A positive OD reading indicates a positive binding response.

The invention also encompasses therapeutic strategies that involve targeting the T cells that are specific for the citrullinated peptide/MHC class II complexes or disrupting the formation of these complexes. These methods may be used in combination with other known therapies for treating RA. For example, the activated T cells may be eliminated by inducing apoptosis of these cells which can be accomplished by administering soluble peptide-MHC class II complexes to a patient (i.e. U.S. Pat. Nos. 5,734,02, 6,106,840, 5,635,363, 6,211,342, U.S. patent application 20020176864 and 20020122818, the disclosures of which are incorporated herein in their entirety). The invention also encompasses the use of the peptides of the invention in therapeutic strategies using methods of RNA interference to modulate T cell activity in a subject. RNA interference (RNAi or siRNA) is a form of gene silencing triggered by double-stranded RNA (dsRNA). In one aspect of the invention using such a method, the peptides of the invention are combined with RNA sequences encoding for example a cytokine that will effect an APC (i.e. dendritic cells) which in turn will affect T cells to shift from an activated inflammatory response to one of a regulatory response. In RNA interference (RNAi), sequence-specific, post-transcriptional gene silencing in animals and plants is initiated by double-stranded RNA (dsRNA) that is homologous in sequence to the silenced gene. A siRNA (small interfering RNA) is designed to target and thus to degrade a desired mRNA (in this case encoding PAD) in order not to express the encoded protein that is involved in citullination of proteins leading to rheumatoid arthritis. Methods relating to the use of RNAi to silence genes in *C. elegans, Drosophila*, plants, and mammals are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366

(2001); Elbashir, S. M., et al., Genes Dev. 15, 188-200 (2001); WO0129058; WO9932619, Elbashir S M, et al., 2001 Nature 411:494-498); and Applicant's Canadian Patent Application 2,388,441 (the disclosures of which are incorporated herein in their entirety).

The invention also encompasses methods of treatment of an autoimmune disorder such as rheumatoid arthritis by the administration of a therapeutic composition comprising one or more peptides according to the invention and a pharmaceutically acceptable carrier to induce systemic immunological tolerance as has been previously described herein. The induced tolerance leads to a reduction of the local inflammatory response in the tissue under attack. In one aspect the peptides can are administered via the mucosal epithelium of patients to induce such systemic immunological tolerance as method is disclosed for example in U.S. Pat. No. 5,843,445 (the disclosure of which is herein incorporated by reference in its entirety).

Still other therapeutic strategies may involve the conjugation of cytotoxic molecules or radioactive molecules labelled with a radionuclide (i.e. $^{125}$I or $^{131}$I) to the peptides of the invention. In other embodiments of the invention are immunotoxin molecules comprising a cell recognition molecule being a peptide or an antibody of the invention covalently bound to a toxin molecule or active fragment thereof. Such immunotoxin molecules may be used alone or provided as a composition for use as a medicament or a diagnostic for rheumatoid arthritis as described herein. Such conjugation of cytotoxic molecules with a peptide of the invention and a MHC class ii molecule is beneficial to target CD4T cells. Alternatively, in aspects, certain of the citrullinated peptides such as that of SEQ ID NO. 38 or 39 can be solely targeted to a cytotoxic molecule to target B cells. In this manner only B cells are targeted that produce the anti-citrulline antibodies having the same antibody on its surface.

In another aspect of the invention, antibodies specific for citrullinated peptide/MHC class II complexes can be used to bind to the complex and thus prevent complex recognition by T cells (i.e. WO 02/14870). Alternatively, the peptide binding groove of the MHC class II molecules may be bound with a high affinity non citrullinated peptide that is not then recognized by the T cell or that is bound by an antibody thus preventing the formation of citrullated peptide/MHC class II complexes (i.e. U.S. Pat. No. 6,355,617).

In a further aspect of the invention, is a method for the diagnosis of an autoimmune disease involving in general, citrullinated peptide antigens evoking a T cell response. Such autoimmune disease includes but is not limited to rheumatoid arthritis and multiple sclerosis. In multiple sclerosis, citrullinated myelin basic protein (MBP) T cell responses have been observed (Tranquil) et al., 2000. Enhanced T cell responsiveness to citrulline-containing myelin basic protein in multiple sclerosis patients. Mult. Scler. 6:4220-5). Therefore in MS patients expressing the MHC class II shared epitope, the immune response to citrulline may contribute to the disease process. As such, the detection of anti-citrulline auto-antibodies to citrullinated MBP may be diagnostic for MS. In aspects, inhibiting T cell reactivity is therapeutic for MS and assaying for this activity is diagnostic for MS. Furthermore, treatments described herein with respect to rheumatoid arthritis are also applicable to the treatment of MS where citrullinated MBP ellicits a T cell response leading to disease. Methods of inhibition of the binding of citrullinated peptides to the shared epitope in susceptible patients (i.e. express the MHC class II shared epitope) as described herein for the treatment of RA may also be applicable to the treatment of MS. Citrullinated MBP peptides useful in the diagnosis of MS and the target of therapeutic methods may be selected for example from FLPCitHRDTG (SEQ ID NO. 40), VTPCitTPPPS (SEQ ID NO. 41); YGGCitASKYK (SEQ ID NO. 42) and LGGCitD-SRSG (SEQ ID NO. 42). Still other citrullinated peptides that may be used in the diagnosis of MS are citrullinated glial fibrillary acid protein (GFAP). GFAP is a protein that is present in glial cells, astrocytes and astroglial filaments (Nicholas A. P. 2002. Preparation of a monoclonal antibody to citrullinated epitopes: its characterization and some applications to immunohistochemistry in human brain. Glia. Mar 15; 37(4):328-36: Nicholas et al., 2003. Immunohistochemical localization of citrullinated proteins in adult rat brain. J Comp Neurol. May 5:459(3):251-66). Citrullinated GFAP for use in methods of diagnosis of MS may be selected MERCitRITSA (SEQ ID NO. 44), LPTCitVDFSL (SEQ ID NO. 45), LNDCitFASYI (SEQ ID NO. 46), LRLCitLDQLT (SEQ ID NO. 47), LQICitETSLD (SEQ ID NO. 48) and VEMCitDGEVI (SEQ ID NO. 49).

It is understood by one of skill in the art that the citrullinated MBP and GFAP of the invention are for use in diagnostic and therapeutic approaches for multiple sclerosis.

Alternatively, in an embodiment of the invention, the modification of certain peptides having arginine to that of citrulline may be prevented by the use of antagonists and/or inhibitors to the enzyme peptidylarginine deiminase (PAD) that catalyzes this amino acid reaction. PAD is a member of a family of enzymes that share similar catalytic activity. These are calcium dependent enzymes and they exist in 4 isoforms in mammalian tissue: PAD I and III are present in hair follicles and epidermis; PAD II is present in CNS tissues, muscle and some hematopoietic cells; PAD IV is present in hematopoietic tissue, particularly monocytes and neutrophils (Vossenaar E. R. et. Al., (2003). PAD, a growing family of citrullinating enzymes; genes, features and involvement in disease. Bioessays. 25(11): 1106-18). The physiologic function of PAD is not completely known, however, is does act to convert the positive charge of arginine to a polar amino acid citrulline with a reduced charge (FIG. 4).

The gene for PAD is present on chromosome 1p36 in humans and 4E1 in mice. While a region on chromosome 1p36 has been previously identified to be associated with rheumatoid arthritis, this region contains four genes in addition to the four PAD genes and there has not been any direct association between PAD activity, increased citrullination of peptides or binding to any HLA-DR molecules leading to the development of rheumatoid arthritis.

Blocking the citrullination in vitro and in vivo of PAD provides a novel therapeutic method for treating rheumatoid arthritis and multiple sclerosis as this focuses on influencing a specific critical step in the disease process. In one aspect of this embodiment of the invention, PAD activity can be blocked using the highly specific and efficient technique of RNA interference (siRNA) discussed briefly supra. In this manner, the function of the PAD gene can be silenced such that citrullination of susceptible peptides/proteins doesn't occur and lead to the development of rheumatoid arthritis or multiple sclerosis. This provides a method of treatment of individuals expressing the SE and PAD who are particularly at risk of developing an autoimmune disease as a result of the production of citrullinated peptides. Both early and later stages of the autoimmune disease, dependent on the production of citrulline, may be suppressed by inhibition of PAD expression and in some aspects of the invention, the suppression of PAD IV expression.

In addition to silencing the expression and thus function of the PAD gene, small molecules may also be used to inhibit PAD and thus such small molecules can also be used in therapeutic compositions for the treatment of autoimmune disorders in various routes of administration. A discussion of compositions and routes of administration of compositions has previously been provided in the description. One of skill in the art would have the understanding and knowledge of how to screen potential small molecules for their capability of inhibiting PAD. Suitable screening methods are described for example in Walters et al., (Designing Screens: How to Make Your Hits a Hit. Nature Reviews, Drug Discovery. Volume 2, April 2003, pgs. 259-266; the disclosure of which is incorporated herein by reference in its entirety).

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of synthetic chemistry, protein and peptide biochemistry, molecular biology, pharmacology and immunology referred to but not explicitly described in this disclosure and examples are reported in the scientific literature and are well known to those skilled in the art.

Example 1

Generation of Animals

HLA-DR4-IE transgenic, murine MHC class II deficient mice were used in these experiments (Ito K, Bian H J, Molina M, Han J, Magram J, Saar E, Belunis C, Bolin D R, Arceo R, Campbell R, Falcioni F, Vidovic D, Hammer J, Nagy Z A. 1996. HLA-DR4-IE chimeric class II transgenic, murine class II-deficient mice are susceptible to experimental allergic encephalomyelitis. *J. Exp. Med.* 183:2635). These mice were bred and maintained as previously described (Hill, J. A., Wang, D., Jevnikar, A. M., Cairns, E., Bell, D. A. 2002. The relationship between predicted peptide-MHC class II affinity and T cell activation in a HLA-DRβ1*0401 MHC class II mouse model. *Arthritis Res.* 5:R40).

Example 2

Generation of Peptides

Peptides used in these studies were synthesized and purified by the manufacturer (Genemed Synthesis, San Francisco, Calif.). Peptides were selected based on their predicted affinity for DRB1*0401 according to the method of Hammer et al (Hammer J, Bono E, Gallazzi F, Belunis C, Nagy Z, Sinigaglia F. 1994. Precise prediction of major histocompatibility complex class II-peptide interaction based on peptide side chain scanning. *J. Exp. Med.* 180: 2353). Underlined amino acids indicate the residues interacting with the nine MHC class II binding pockets (P1-P9), while those that appear in bold interact at the P4 shared epitope position. The sequences of the peptides used from the proteoglycan aggrecan are as follows: P4D=human aggrecan peptide 280-292, AGWLADRSVRYPI (SEQ ID NO. 62); P4R=altered human aggrecan peptide 280-292, AGWLARRSVRYPI (SEQ ID NO. 63); P4Cit=altered human aggrecan peptide 280-292, AGWLACitRSVRYPI (SEQ ID NO. 64). Since citrulline is not accounted for in the predictive algorithm of Hammer et al. the value of glutamine was substituted for arginine when identifying a candidate T cell epitope from vimentin (glutamine has the same terminal side-chain group as citrulline). The sequences of the vimentin peptides used are as follows: Vim 65-77=human vimentin peptide 65-77, SAVRARSSVPGVR (SEQ ID NO. 65), Vim R70Cit=altered human vimentin peptide 65-77, SAVRACitSSVPGVR (SEQ ID NO. 66).

Example 3

Immunizations

DR4 tg mice were immunized intradermally at the interior side of both hind legs with 100 µl of peptide (1 µg/µl) emulsified in CFA (Difco Laboratories, Detroit, Mich.) in a 1:1 volume ratio. After 10 days, mice were sacrificed and their draining lymph nodes were removed for in vitro proliferation and cytokine assays.

Example 4

T Cell Cultures

Cell suspensions were prepared from the draining lymph nodes and cultured in 96-well plates at a concentration of $4 \times 10^5$ cells/well in the presence or absence of peptide antigen for 4 days. Anti-DR antibody (BD PharMingen, Mississauga, ON) was added to some cultures (1 µg/ml) to confirm DR restricted T cell responses as described previously (Andersson E C, Hansen B E, Jacobsen H, Madsen L S, Andersen C B, Engberg J, Rothbard J B, McDevitt G S, Malmstrom V, Holmdahl R, Svejgaard A, Fugger L. 1998. Definition of MHC and T cell receptor contacts in the HLA-DR4 restricted immunodominant epitope in type II collagen and characterization of collagen-induced arthritis in HLA-DR4 and human CD4 transgenic mice. *Proc. Natl. Acad. Sci. USA.* 95:7574). Culture supernatants were removed after 78 hrs to test IFN-γ production by ELISA (BD PharMingen, Mississauga, ON) as described previously (Hill, J. A., Wang, D., Jevnikar, A. M., Cairns, E., Bell, D. A. 2002. The relationship between predicted peptide-MHC class II affinity and T cell activation in a HLA-DRβ1*0401 MHC class II mouse model. *Arthritis Res.* 5:R40). Cytokine production was measured in duplicate and represents the average antigen specific cytokine production (cytokine production in control samples+2 SD were subtracted from the peptide specific cytokine production)±SD. Eighteen hours before culture termination, 1 µCi of [$^3$H] thymidine (ICN Biomedicals, Montreal, PQ) was added to each well to assess T cell proliferation. Proliferation experiments were conducted in triplicate and results are presented as average proliferation in cpm±SD or stimulation index (cpm of experimental sample/cpm of control sample)±SEM.

Example 5

Peptide-Binding Assay

Peptide binding affinity to purified HLA-DRB1*0101, *0401, *0404, *0301, *0701, *0802, *1101, and *1302 molecules was determined relative to radio-labelled peptide probes as described previously (Southwood S, Sidney J, Kondo A, del Guercio M F, Appella E, Hoffman S, Kubo R T, Chesnut R W, Grey H M, Sette A. 1998. Several common HLA-DR types share largely overlapping peptide binding repertoires. *J. Immunol.* 160:3363). The nM concentration of unlabelled vimentin peptide necessary for 50% inhibition of the labelled peptide to the purified HLA-DRB1 molecules (IC$_{50}$) was used as an approximation of the affinity of interaction (kDa). Results are expressed as the inverse of the IC$_{50}$ values measured in nM.

Example 6

Induction of Arthritis in DR4-IE Tg Mice

DR4-IE tg mice were immunized subcutaneously at the interior side of both hind legs with 100 µl of citrullinated human fibrinogen (1 µg/µl) emulsified in CFA (Difco Laboratories, Detroit, Mich.) in a 1:1 volume ratio. Citrullinated fibrinogen was prepared as described previously (Christine Masson-Bessiere et al., 2001. The Major Synovial Targets of the Rheumatoid arthritis-Specific Antifilaggrin Autoantibodies Are Deiminated Forms of the α and β Chains of Fibrin 1 *The Journal of Immunology* 166: 4177-4184). Mice received a second immunization of the same antigen in incomplete Freund's adjuvant 21 days and were subsequently observed for signs of arthritis (FIGS. 6A-F).

Example 7

Figure 7:
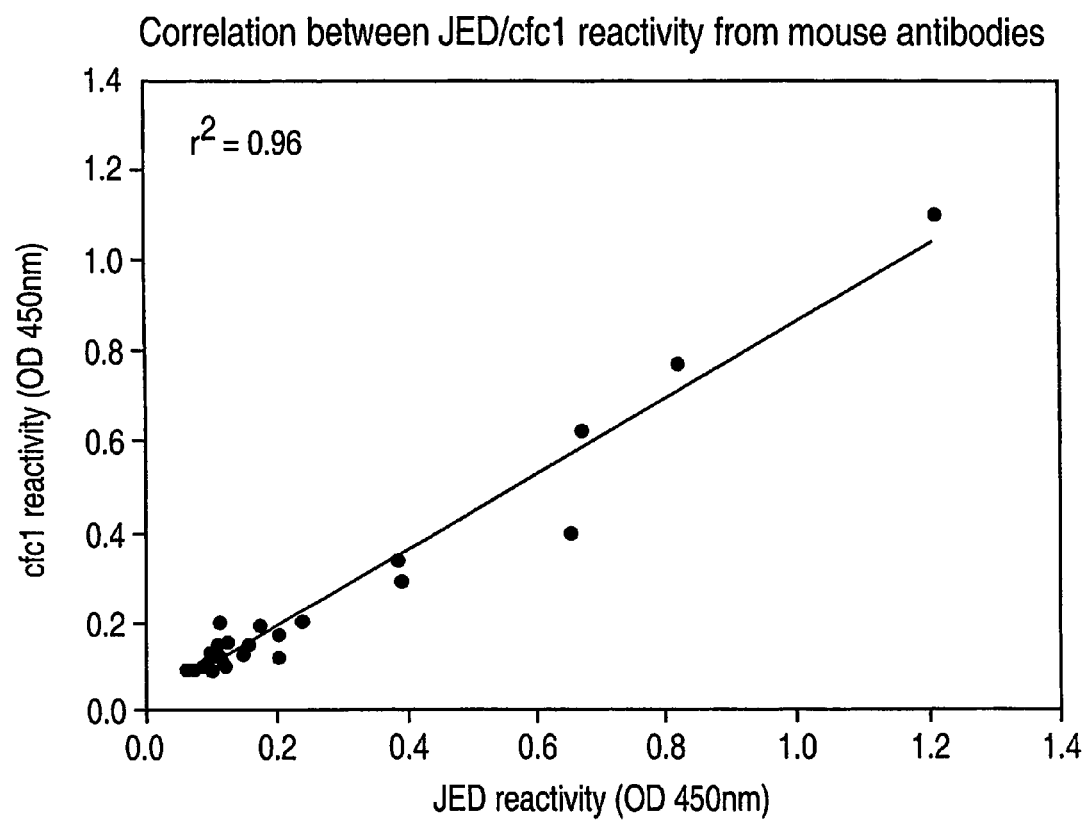
FIG. 7 shows the production of anti-citrulline antibodies in DR4-IE tg mice.

Generation of Anti-Citrulline Antibodies in DR4-IE Tg Mice and Detection of RA Autoantibodies DR4-IE tg mice were immunized at days 0, 21 and 42 with 100 µg of the peptide Cit-Cit-Y-Cit-G-Cit-Cit-S-Cit-Cit-S-Cit-Cit (SEQ ID NO. 39) emulsified in CFA, IFA and IFA respectively. At day 52 mice were sacrificed and serum was collected from blood. Antibody reactivity was detected in the serum samples by ELISA using the peptide (SEQ ID NO. 39) and the cfc1 peptide described previously (Schllekens et al., 1998. J Clin Invest. Volume 101, Number 1, January 1998, pp. 273-281). Anti-citrulline antibodies to the peptide (SEQ ID NO. 39) or cfc1 were found in the serum of mice that were immunized with the peptide (SEQ ID NO. 39). Antibodies from arthritic mice immunized with citrullinated fibrinogen also bound both of these peptides. No antibodies were seen in a number of control mice tested. Human antibody reactivity against peptide Cit-Cit-Y-Cit-G-Cit-Cit-S-Cit-Cit-S-Cit-Cit (SEQ ID NO. 39) was also tested and compared to a commercial ELISA kit (Quantilite, INOVA Diagnostics). Antibody reactivity to citrullinated fibrinogen was also demonstrated (FIG. 7).

Table 1 shows the frequency and specificity of anti-citrulline antibodies using the peptide Cit-Cit-Y-Cit-G-Cit-Cit-S-Cit-Cit-S-Cit-Cit (SEQ ID NO. 39), a citrullinated fibrinogen polypeptide (previously used to immunize transgenic mice) and the commercial CCP reagent. The sensitivity and specificity of this assay for rheumatoid arthritis amongst the patients tested is shown and indicates that the Cit-Cit-Y-Cit-G-Cit-Cit-S-Cit-Cit-S-Cit-Cit (SEQ ID NO. 39) peptide and CCP peptide were similar in terms of their sensitivity and specificity for the diagnosis of RA.

Figure 8:
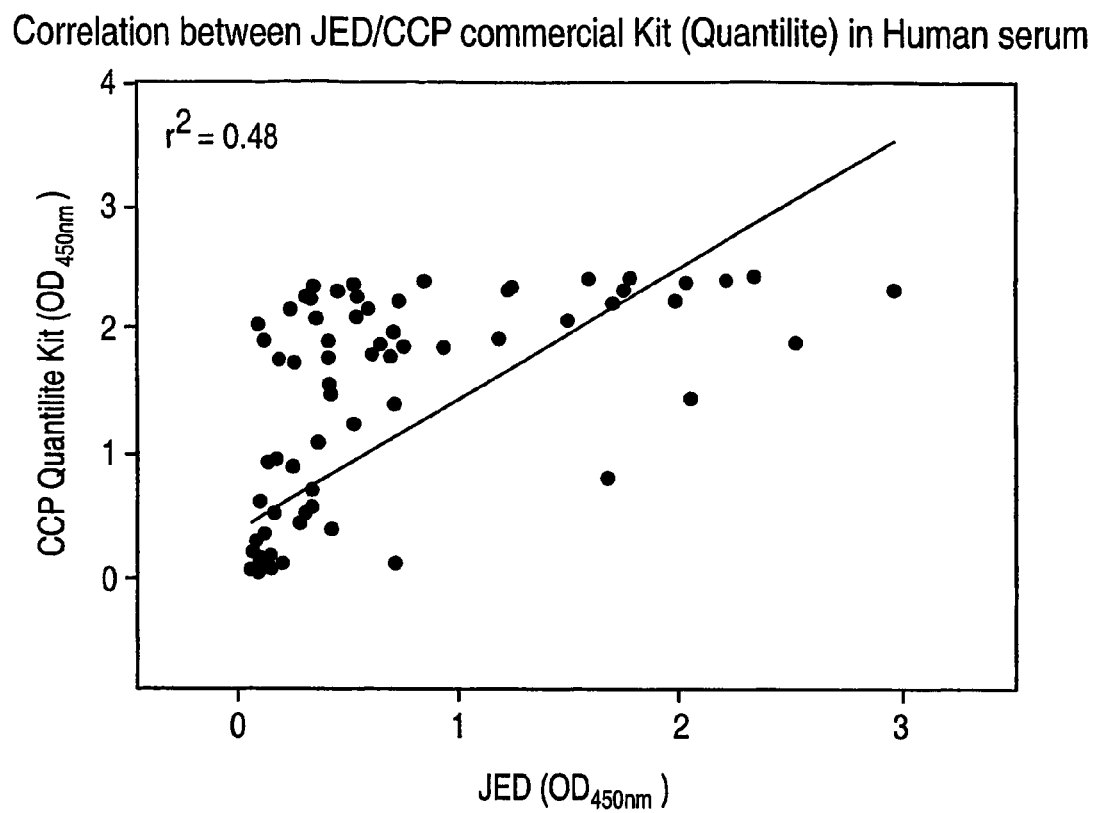
FIG. 8 shows the correlation between peptide Cit-Cit-Y-Cit-G-Cit-Cit-S-Cit-Cit-S-Cit-Cit (SEQ ID NO. 39) and CCP using a commercial kit (Quantilite™) in human serum.

FIG. 8 shows the correlation of anti-citrulline antibodies using the commercial CCP kit and the Cit-Cit-Y-Cit-G-Cit-Cit-S-Cit-Cit-S-Cit-Cit (SEQ ID NO. 39) peptide. From the 51 rheumatoid arthritis patients tested using these assays, a correlation co-efficient of 0.48 was seen. As seen in Table 2, the peptide Cit-Cit-Y-Cit-G-Cit-Cit-S-Cit-Cit-S-Cit-Cit (SEQ ID NO. 39) provided a specificity of 98% and sensitivity of 71% for the diagnosis of rheumatoid arthritis. Only 1 out of 49 patients with psoriatic arthritis was positive. This indicates that the peptide Cit-Cit-Y-Cit-G-Cit-Cit-S-Cit-Cit-S-Cit-Cit (SEQ ID NO. 39) and in general peptides of the formula: Cit-Cit-X-Cit-G-Cit-Cit-Z-Cit-Cit-B-Cit-Cit (SEQ ID NO. 38), wherein X is selected from Y, F, W, I, L, M and V; Z is selected from A, D, I, N, P, S, T, V; and B is selected from A, G, H, Q, S, T and V is useful for the detection of anti-citrulline antibodies in rheumatoid arthritis.

Example 8

Inhibition of PAD using siRNA, in vitro studies for selection of mouse and human cell lines for PAD expression; to identify siRNA(s) for PAD targeting; to inhibit PAD expression in selected cell lines using siRNA(s); and to monitor PAD expression. While described with respect to PAD IV, similar processes can be used for PAD II or any other PAD as is understood by one of skill in the art.

(a) Selection of Mouse and Human Cell Lines for PAD (II and IV) Expression

Human and mouse monocyte/macrophage and granulocyte/neutrophil cell lines from ATCC (Table 3). These cell lines can be further differentiated to macrophage and neutrophil phenotypes using a variety of agents such as vitamin D3, retinoic acid and dexamethasone. Neutophil and macrophage cell types express PAD II and IV (Asaga H, et al., (1998) Selective deimination of vimentin in calcium ionophore-induced apoptosis of mouse peritoneal macrophages. Biochem Biophys Res Commun. 243(3):641-6: Nakashima K, et al., (1999) Molecular characterization of peptidylarginine deiminase in HL-60 cells induced by retinoic acid and 1alpha,25-dihydroxyvitamin D3. J Biol Chem. 274(39), 27786-92). The cells are activated and abundant in RA synovium. PAD II and IV will be quantitively determined in LPS activated cell lines and those cell lines with the highest level of PAD II and IV is selected to test siRNA inhibition.

(b) Identification of siRNA(s) for PAD (II and IV) Targeting

Analysis of the human and mouse PAD IV gene sequence revealed a total of eleven siRNA sequences that fulfil the selection criteria. Of the eleven sequences, 8 were human and 3 were mouse (Table 4). These siRNAs will be obtained from Dharmacon Inc. which uses a proprietary RNA modification called siSTABLE technology that enhances siRNA stability, longevity and potency.

(c) Inhibition of PAD (II and IV) Expression siRNAs will be tested in selected high PAD II or IV expressing human and mouse cell lines in order to establish the optimal conditions for effective PAD II or IV inhibition in these cells. This is dependent on siRNA delivery, dosages and timing. SiRNA will be delivered to the cells by liposomal transfection which is a technique well known to those of skill in the art. Several cationic liposome reagents (Table 5) will be employed since transfection efficiency may vary depending on the cell type used. Transfection efficiency and toxicity will be monitored by FACS using fluorescently labeled siRNA (FL Luciferase GL2 Duplex) and propidium iodide staining, respectively. The use of immunoliposomes, which contain cell marker specific antibodies in the cationic lipid complex, should allow for the efficient targetting of the siRNA to either macrophages or neutrophils that produce PAD IV (Zhang Y, et al., (2003) In vivo knockdown of gene expression in brain cancer with intravenous RNAi in adult rats. J Gene Med. 5(12):1039-45: Bestman-Smith J. et al., (2000) Sterically stabilized liposomes bearing anti-HLA-DR antibodies for targeting the primary cellular reservoirs of HIV-1. Biochim Biophys Acta. 1468(1-2):161-74).

(d) Monitoring of PAD (II and IV) Expression

PAD II or IV mRNA and protein expression in non-treated versus siRNA-treated cells will be monitored by RT-PCR and Western blotting respectively. The use of these methods in combination is best for analyzing siRNA mediated inhibition. The oliogonucleotide primers employed in the PCR are listed in Table 6 and Table 7. These include primers for GAPDH, PAD I, II and III in addition to PAD IV since gene expression of a housekeeping gene and all PADs will assure target specificity for the siRNA therapy. Polyclonal anti-PAD IV antibodies that recognize both human and mouse protein are obtained as are recombinant PAD IV to use as a standard.

Example 8

Inhibition of PAD using siRNA, in vivo studies to demonstrate the delivery of siRNA therapy; to select animal models for siRNA therapy; and to monitor the effects of PAD IV inhibition.

(a) Delivery of siRNA Therapy

Liposome/immunoliposome siRNA complexes identified in vitro as the most effective and specific PAD II and IV inhibitors are to be intravenously injected. This approach has been shown previously to effectively inhibit gene expression in a number of organs including liver, lung, kidney, spleen and pancreas (Lewis D. L. et al., (2002) Efficient delivery of siRNA for inhibition of gene expression in postnatal mice. Nat Genet. 32(1): 107-8; Song E. et al., (2003) RNA interference targeting Fas protects mice from fulminant hepatitis. Nat Med. 9(3): 347-51). Retroviral delivery of plasmid encoded siRNA may also be used as an alternative approach (McCaffrey A. P. et al., (2002) RNA interference in adult mice. Nature 418(6893):38-9).

(b) Selection of Animal Models for siRNA Therapy

Several mouse models of arthritis will be used. The first is streptococcal cell (SCW) induced arthritis, which is an acute arthritis model in which arthritis is induced within 24 hours with concomitant upregulation of PAD IV within the joints of the mice (Vossenaar E. R. et al., (2003) Citrullination of synovial proteins in murine models of rheumatoid arthritis. Arthritis Rheum. 48(9): 2489-500). The determination of optimal conditions for siRNA therapy including delivery and dose is shown in Table 8. The second model, collagen induced arthritis (CIA) is chronic with persistent arthritis onsetting 35 days post-immunization. This allows for the monitoring of siRNA effects over an extended period of time (Table 9). The SCW and CIA mouse models will show increased levels of PAD IV activity and the presence of citrullinated proteins in the joints of these mice, however, there is no autoimmune response targeted to citrulline. When SCW arthritis is induced in SE tg mice, an autoimmune response to citrulline occurs as SE tg mice develop arthritis when immunized with citrulline. This will prolong and/or worsen the transient arthritis normally expected with SCW in non-SE tg wild type mice (Table 10). This effect is dampened by PAD IV inhibition.

(c) Monitoring the Effects of siRNA Therapy

The siRNA/liposome treated and non-treated mice will be sacrificed at various time points to determine the efficacy and duration of siRNA therapy. This will be assessed by monitoring the clinical signs of arthritis using a standard scoring system (Current Protocols in Immunology Chapter 15.5). Also monitored will be the pathological signs of disease and the process of citrullination. Sectioned joints will be scored for inflammation and the presence of citrullinated proteins, PAD IV protein and its transcript. The production of anti-citrulline antibodies will also be assessed in the SE tg mouse models.

Although preferred embodiments of the invention have been described herein in detail, it will be understood by those skilled in the art that variations may be made thereto without departing from the spirit of the invention or the scope of the appended claims.

TABLE 1

| Diagnosis | Number | JED | CitFIb | CCP |
|---|---|---|---|---|
| Rheumatoid Arthritis | 74 | 49 | 43 | 48 |
| Other rheumatic diseases | 48 | 3 | 2 | 4 |
| Arthritis | 5 | 0 | 0 | 0 |
| Connective Tissue Disease | 1 | 0 | 0 | 0 |
| Fibromyalgia | 2 | 0 | 0 | 0 |
| Hepatitis C Virus infection | 2 | 0 | 0 | 0 |
| Inflammatory Bowel disease | 1 | 0 | 0 | 0 |
| Mixed Connective Tissue Disease | 1 | 0 | 0 | 0 |
| Osteoarthritis | 4 | 0 | 0 | 0 |
| Overlap Syndrome | 2 | 1 | 1 | 1 |
| Primary Billary Cirhosis | 1 | 1 | 0 | 1 |
| Polymyalgia Rheumatica | 6 | 0 | 0 | 0 |
| Psoriasis | 3 | 0 | 0 | 0 |
| Reiters Syndrome | 1 | 0 | 0 | 0 |
| Sarcoidosis | 1 | 0 | 0 | 0 |
| Scleroderma | 1 | 0 | 0 | 0 |
| Sjogren's Syndrome | 4 | 0 | 0 | 0 |
| Systemic Lupus Erythematosus | 4 | 0 | 0 | 0 |
| Spondyloarthropathy | 2 | 0 | 0 | 1 |
| Undifferentiated Connective Tissue Disease | 3 | 1 | 1 | 1 |
| Vasculitis | 4 | 0 | 0 | 0 |

| Test | Sensitivity (%) | Specificity (%) |
|---|---|---|
| JED | 66 | 94 |
| CitFIb | 58 | 96 |
| CCP | 65 | 92 |

Below you can see the correlation between antibody reactivity to the JED antigen and the CCP antigen in human serum samples.

TABLE 2

| Patients | Number | JED positive | Sensitivity (%) | Specificity (%) |
|---|---|---|---|---|
| Rheumatoid Arthritis | 51 | 36 | 71 | 98 |
| Psoriatic Arthritis | 49 | 1 | | |

TABLE 3

Human and mouse cell lines to be tested in this study.

| Name | Cell Type | Origin |
|---|---|---|
| HL-60 | Monocyte/Macrophage | Human |
| HL-60 | Neutrophil/Granulocyte | Human |
| THP-1 | Monocyte/Macrophage | Human |
| MPRO 2.1 | Neutrophil/Granulocyte | Mouse |
| M1 | Monocyte/Macrophage | Mouse |

All cell lines are either currently being used in our lab or can be ordered from ATCC. Differentiation to a macrophage or neutrophil phenotype is required for these cell lines (e.g. retinoic acid, vitamin D3, LPS).

TABLE 4 siRNA sequences selected for this study.

| Gene | Sequence | Start Site[1] | GC Content (%) |
|---|---|---|---|
| Human PAD IV | GGTTCAGATTTCATACTAC (SEQ ID NO. 83) | 299 | 37 |

TABLE 4-continued siRNA sequences selected for this study.

| Gene | Sequence | Start Site[1] | GC Content (%) |
|---|---|---|---|
| Human PAD IV | ACCAGAGCTGTGAAAGATC (SEQ ID NO. 84) | 414 | 47 |
| Human PAD IV | CCAGAGCTGTGAAAGATCA (SEQ ID NO. 85) | 415 | 47 |
| Human PAD IV | CTGCGAGGATGATGAAGTG (SEQ ID NO. 86) | 521 | 53 |
| Human PAD IV | GGTGTACGCGTGCAGTATT (SEQ ID NO. 87) | 947 | 53 |
| Human PAD IV | CTACTCTGGCCATGAAAGC (SEQ ID NO. 88) | 997 | 53 |
| Human PAD IV | GGTCCTGCTACAAACTGTT (SEQ ID NO. 89) | 1510 | 47 |
| Human PAD IV | GTTCTCTAAGGCGGAAGCT (SEQ ID NO. 90) | 1751 | 53 |
| Mouse PAD IV | AGATGAACAAAGTGAGAGT (SEQ ID NO. 91) | 636 | 37 |
| Mouse PAD IV | GACAATCAATGAAATTCTG (SEQ ID NO. 92) | 1585 | 32 |
| Mouse PAD IV | TCAACGACTTCTACACCTA (SEQ ID NO. 93) | 1914 | 42 |
| FL Luciferase GL2 Duplex[3] | CGTACGCGGAATACTTCGA (SEQ ID NO. 94) | N/A | 53 |
| Luciferase GL2 Duplex | CGTACGCGGAATACTTCGA (SEQ ID NO. 95) | N/A | 53 |

[1]Start Site indicates the nucleotide within the mRNA where the siRNA sequence originates;
[2]Optimal GC content for siRNA is 50%.
[3]Luciferase GL2 Duplex is a pre-synthesized siRNA produced by Dharmacon for use as a control. Fluorescein labelled (FL) Luciferase GL2 Duplex will be used to determine siRNA transfection efficiencies in vitro and in vivo by FACS.
Detail on the selection of siRNA sequences can be found at: http://design.dharmacon.com/rnadesign/help/selction.htm.

TABLE 5

Transfection reagents that will be used in this study.

| Name | Supplier |
|---|---|
| Immunoliposome* | Avanti Polar Lipids |
| Lipofectamine | Invitrogen |
| Oligofectamine | Invitrogen |
| Geneporter | Gene Therapy Systems |
| siPORT | Ambion |

*Immunoliposomes are streptavidin coated cationic lipids. These can be used in combination with biotin labelled antibodies for cell specific targeting of siRNA.

TABLE 6

Primers for analyzing siRNA mediated inhibition of PAD IV mRNA.

| siRNA target | Left sequence | Right sequence | Product size |
|---|---|---|---|
| Human PAD IV 299, 414, 415 | 195- CCAGCCAAGAAGAAATCCAC (SEQ ID NO. 67) | 424- ACAGCTCTGGTTGGCTTCAC (SEQ ID NO. 68) | 230 |
| Human PAD IV 521 | 472- TCCTGCTGGTGAACTGTGAC (SEQ ID NO. 69) | 716- ACCCAAGACTACGCTGCACT (SEQ ID NO. 70) | 245 |
| Human PAD IV 947, 997 | 884- GGCTCATTACCCTCACCATC (SEQ ID NO. 71) | 1097- AGCTTGCACTTGGCTTTCAT (SEQ ID NO. 72) | 280 |
| Human PAD IV 1510 | 1441- TGGACGAGTTCCTGAGCTTT (SEQ ID NO. 73) | 1667- GTCGATGCATCTCTCCACAA (SEQ ID NO. 74) | 227 |

TABLE 6-continued

Primers for analyzing siRNA mediated inhibition of PAD IV mRNA.

| siRNA target | Left sequence | Right sequence | Product size |
|---|---|---|---|
| Human PAD IV 1751 | 1565- GCTGTTCGAAGGGATCAAGA (SEQ ID NO. 75) | 1808- CTTCCCTAGCACCAGCATGT (SEQ ID NO. 76) | 244 |
| Mouse PAD IV 636 | 547- GCAGGACATGTCTCCAATGA (SEQ ID NO. 77) | 735- AGCTCCAGGCAATACGAGAA (SEQ ID NO. 78) | 189 |
| Mouse PAD IV 1585 | 1550- GCGACACTGTTCGAAGGACT (SEQ ID NO. 79) | 1762- GGCCTTAGAGTTCCCTCTGG (SEQ ID NO. 80) | 213 |
| Mouse PAD IV 1914 | 1767- CCTTCTTCCCAAACATGGTG (SEQ ID NO. 81) | 2007- ATGTGCCACCACTTGAAGGT (SEQ ID NO. 82) | 241 |

Primers were designed using Primer3 and selected to flank the siRNA targeted sequences.

TABLE 7

Other PCR primers

| | NBCI accession number | Left sequence | Right sequence | Product size (bp) |
|---|---|---|---|---|
| Human | | | | |
| PAD I | NM_013358 | 236-CATGGTCTACAACCGCACAC (SEQ ID NO. 96) | 564-CCTGTGATTGTCCCGGTCAC (SEQ ID NO. 97) | 328 |
| PAD II | NM_007365 | 651-CCGGATACGAGATAGTTCTG (SEQ ID NO. 98) | 1118-ATCCTGGATCCAGCGATCGC (SEQ ID NO. 99) | 467 |
| PAD III | NM_016233 | 358-CCTATGCGGTGCTCTACCTC (SEQ ID NO. 100) | 524-CAGCTCGGATCATCACGGTC (SEQ ID NO. 101) | 166 |
| GAPDH (control) Stratagene | | CCACCCATGGCAAATTCCATGGCA (SEQ ID NO. 102) | TCTAGACGGCAGGTCAGGTCCACC (SEQ ID NO. 103) | 600 |
| Mouse | | | | |
| PAD I | NM_011059 | 626-TGCTAACCATTTGAAG (SEQ ID NO. 104) | 1085-TTGTCATTGCGGCCGTGG (SEQ ID NO. 105) | 459 |
| PAD II | NM_008812 | 571-CATGTCTCAGATGATCCT (SEQ ID NO. 106) | 744-CGTGGTAGAGCTTCTGCC (SEQ ID NO. 107) | 173 |
| PAD III | NM_011060 | 415-CTGTGCGGACCGGCAGG (SEQ ID NO. 108) | 727-CACACTTATAGGCCTCACAG (SEQ ID NO. 109) | 312 |
| GAPDH (control) | | TGATGACATCAAGAAGGTGGTGAAG (SEQ ID NO. 110) | TCCTTGGAGGCCATGTAGGCCAT (SEQ ID NO. 111) | 300 |

TABLE 8

Scheme for determining the most effective dose of siRNA

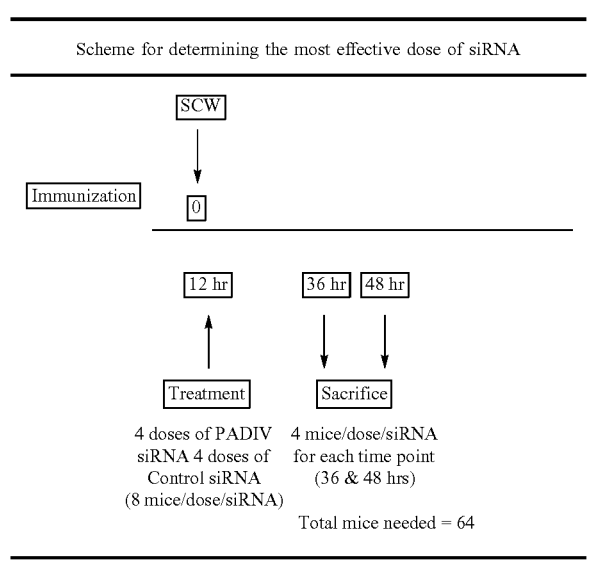

4 doses of PADIV siRNA 4 doses of Control siRNA (8 mice/dose/siRNA)

4 mice/dose/siRNA for each time point (36 & 48 hrs)

Total mice needed = 64

TABLE 9

Scheme for determining the most effective siRNA dosing regime

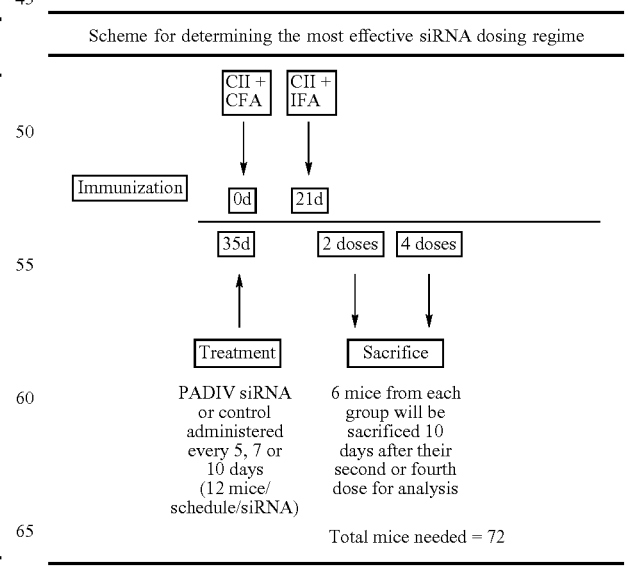

PADIV siRNA or control administered every 5, 7 or 10 days (12 mice/schedule/siRNA)

6 mice from each group will be sacrificed 10 days after their second or fourth dose for analysis Total mice needed = 72

TABLE 10

Scheme for analyzing autoimmune responses in SE tg mice after PADIV siRNA treatment

```
                    SCW
                     │
  Immunization       ▼
                    [0]
                     │
          ┌──────────┼──────────┐
          ▼          ▼          ▼
         [1d]      [21d]      [42d]
          ▲          │          │
          │          ▼          ▼
      Treatment   Sacrifice Optimal dose and      8 mice/siRNA
   treatment regime      for each time point
       for PADIV            (21 & 42d)
   siRNA and control     Serum will be
    (16 mice/siRNA)      analyzed for anti-
                         citrulline antibodies
                         Total mice needed = 32
```

The invention claimed is:

1. A peptide comprising the sequence: Cit-Cit-Y-Cit-G-Cit-Cit-S-Cit-Cit-S-Cit-Cit (SEQ ID NO. 39), wherein the peptide is circularized.

2. The peptide of claim 1, wherein said peptide is labelled with a detectable label.

3. The peptide of claim 1, wherein said peptide is conjugated to a cytotoxic molecule or radioactive molecule.

4. The peptide of claim 1, further comprising cysteines added to one or both ends of the peptide to circularize the peptide by the formation of disulfide bonds.

5. The peptide of claim 1, further comprising a charged amino acid at the beginning and/or end of SEQ ID NO:39.

6. The peptide of claim 5, further comprising cysteines added to one or both ends of the peptide to circularize the peptide by the formation of disulfide bonds.

7. The peptide of claim 1, wherein the peptide is up to 55 amino acids in length.

8. The peptide of claim 1,
wherein the peptide comprises a charged amino acid at the beginning and/or end of SEQ ID NO. 39,
wherein the peptide further comprises cysteines added to one or both ends of the peptide to circularize the peptide by the formation of disulfide bonds, and
wherein the peptide is up to 20 amino acids in length.

* * * * *

SEQUENCE LISTING

```
<160> NUMBER OF SEQ ID NOS: 109

<210> SEQ ID NO 1
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is Cit

<400> SEQUENCE: 1

Ser Ala Val Arg Ala Xaa Ser Ser Val Pro Gly Val Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 2

Phe Ser Met Xaa Ile Val Cys Leu Val
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit
```

```
<400> SEQUENCE: 3

Val Val Glu Xaa His Gln Ser Ala Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 4

Phe Thr Asn Xaa Ile Asn Lys Leu Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 5

Leu Arg Ser Xaa Ile Glu Val Leu Lys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 6

Val Leu Lys Xaa Lys Val Ile Glu Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 7

Ile Lys Ile Xaa Ser Cys Arg Gly Ser
1               5

<210> SEQ ID NO 8
<211> LENGTH: 9
<212> TYPE: PRT
<213> ORGANISM: Artificial Sequence
<220> FEATURE:
```

<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 8

Leu Pro Ser Xaa Asp Arg Gln His Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 9

Phe Arg His Xaa His Pro Asp Glu Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 10

Phe Pro Ser Xaa Gly Lys Ser Ser Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 11

Ile Gln Gln Xaa Met Asp Gly Ser Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 12

Leu Thr Gln Xaa Gly Ser Val Leu Arg
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 13

Tyr His Phe Xaa Val Gly Ser Glu Ala
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 14

Tyr Asp Pro Xaa Asn Asn Ser Pro Tyr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 15

Val Ser Phe Xaa Gly Ala Asp Tyr Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 16

Tyr Ser Leu Xaa Ala Val Arg Met Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

```
<400> SEQUENCE: 17

Met Lys Ile Xaa Pro Leu Val Thr Gln
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 18

Tyr Arg Ala Xaa Pro Ala Lys Ala Ala
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 19

Trp Gln Lys Xaa Gln Lys Gln Val Lys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 20

Ile Gln Asn Xaa Gln Asp Gly Ser Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 21

Trp Tyr Asn Xaa Cys His Ala Ala Asn
1               5

<210> SEQ ID NO 22
<211> LENGTH: 9
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 22

Tyr Ser Met Xaa Lys Met Ser Met Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 23

Met Lys Ile Xaa Pro Phe Phe Pro Gln
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 24

Leu His Pro Xaa Asn Leu Ile Leu Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 25

Val Ala Thr Xaa Asp Asn Cys Cys Ile
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 26

Leu Asp Glu Xaa Phe Gly Ser Tyr Cys
1               5
```

```
<210> SEQ ID NO 27
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 27

Leu Lys Ser Xaa Ile Met Leu Glu Glu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 28

Phe Gln Lys Xaa Leu Asp Gly Ser Val
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 29

Tyr Ala Leu Xaa Val Glu Leu Glu Asp
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 30

Trp Asn Gly Xaa Thr Ser Thr Ala
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
```

<223> OTHER INFORMATION: Xaa is Cit

<400> SEQUENCE: 31

Trp Lys Thr Xaa Trp Tyr Ser Met Lys
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 32

Tyr Ala Thr Xaa Ser Ser Ala Val Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 33

Val Arg Leu Xaa Ser Ser Val Pro Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 34

Leu Asn Asp Xaa Phe Ala Asn Tyr Ile
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 35

Met Leu Gln Xaa Glu Glu Ala Glu Asn
1               5

<210> SEQ ID NO 36
<211> LENGTH: 9
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 36

Leu Asn Leu Xaa Glu Thr Asn Leu Asp
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 37

Val Glu Thr Xaa Asp Gly Gln Val Ile
1               5

<210> SEQ ID NO 38
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Cit
<220> FEATURE:
<221> NAME/KEY: MISC_FEATURE
<222> LOCATION: (2)..(2)
<223> OTHER INFORMATION: Xaa is Cit
<220> FEATURE:
<221> NAME/KEY: MISC_FEATURE
<222> LOCATION: (3)..(3)
<223> OTHER INFORMATION: Xaa is Tyr, Phe, Trp, Ile, Leu, Met or Val
<220> FEATURE:
<221> NAME/KEY: MISC_FEATURE
<222> LOCATION: (4)..(4)
<223> OTHER INFORMATION: Xaa is Cit
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (8)..(8)
<223> OTHER INFORMATION: Xaa is Ala, Asp, Ile, Asn, Pro, Ser, Thr or Val
<220> FEATURE:
<221> NAME/KEY: MISC_FEATURE
<222> LOCATION: (9)..(9)
<223> OTHER INFORMATION: Xaa is Cit
<220> FEATURE:
<221> NAME/KEY: MISC_FEATURE
<222> LOCATION: (10)..(10)
<223> OTHER INFORMATION: Xaa is Cit
<220> FEATURE:
<221> NAME/KEY: MISC_FEATURE
<222> LOCATION: (11)..(11)
<223> OTHER INFORMATION: Xaa is Ala, Gly, His, Gln, Ser, Thr or Val
<220> FEATURE:
<221> NAME/KEY: MISC_FEATURE
```

```
<222> LOCATION: (12)..(12)
<223> OTHER INFORMATION: Xaa is Cit
<220> FEATURE:
<221> NAME/KEY: MISC_FEATURE
<222> LOCATION: (13)..(13)
<223> OTHER INFORMATION: Xaa is Cit

<400> SEQUENCE: 38

Xaa Xaa Xaa Xaa Gly Xaa Xaa Xaa Xaa Xaa Xaa Xaa Xaa
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Cit
<220> FEATURE:
<221> NAME/KEY: MISC_FEATURE
<222> LOCATION: (2)..(2)
<223> OTHER INFORMATION: Xaa is Cit
<220> FEATURE:
<221> NAME/KEY: MISC_FEATURE
<222> LOCATION: (4)..(4)
<223> OTHER INFORMATION: Xaa is Cit
<220> FEATURE:
<221> NAME/KEY: MISC_FEATURE
<222> LOCATION: (6)..(6)
<223> OTHER INFORMATION: Xaa is Cit
<220> FEATURE:
<221> NAME/KEY: MISC_FEATURE
<222> LOCATION: (7)..(7)
<223> OTHER INFORMATION: Xaa is Cit
<220> FEATURE:
<221> NAME/KEY: MISC_FEATURE
<222> LOCATION: (9)..(9)
<223> OTHER INFORMATION: Xaa is Cit
<220> FEATURE:
<221> NAME/KEY: MISC_FEATURE
<222> LOCATION: (10)..(10)
<223> OTHER INFORMATION: Xaa is Cit
<220> FEATURE:
<221> NAME/KEY: MISC_FEATURE
<222> LOCATION: (12)..(12)
<223> OTHER INFORMATION: Xaa is Cit
<220> FEATURE:
<221> NAME/KEY: MISC_FEATURE
<222> LOCATION: (13)..(13)
<223> OTHER INFORMATION: Xaa is Cit

<400> SEQUENCE: 39

Xaa Xaa Tyr Xaa Gly Xaa Xaa Ser Xaa Xaa Ser Xaa Xaa
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 40

Phe Leu Pro Xaa His Arg Asp Thr Gly
1               5
```

```
<210> SEQ ID NO 41
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 41

Val Thr Pro Xaa Thr Pro Pro Pro Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 42

Tyr Gly Gly Xaa Ala Ser Lys Tyr Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 43

Leu Gly Gly Xaa Asp Ser Arg Ser Gly
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 44

Met Glu Arg Xaa Arg Ile Thr Ser Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit
```

```
<400> SEQUENCE: 45

Leu Pro Thr Xaa Val Asp Phe Ser Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 46

Leu Asn Asp Xaa Phe Ala Ser Tyr Ile
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 47

Leu Arg Leu Xaa Leu Asp Gln Leu Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 48

Leu Gln Ile Xaa Glu Thr Ser Leu Asp
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is Cit

<400> SEQUENCE: 49

Val Glu Met Xaa Asp Gly Glu Val Ile
1               5

<210> SEQ ID NO 50
<211> LENGTH: 9
<212> TYPE: PRT
<213> ORGANISM: Artificial Sequence
<220> FEATURE:
```

```
<223> OTHER INFORMATION: Nucleophosmin/B23 Peptide

<400> SEQUENCE: 50

Leu Ser Leu Arg Thr Val Ser Leu Gly
1               5

<210> SEQ ID NO 51
<211> LENGTH: 9
<212> TYPE: PRT
<213> ORGANISM: Artificial Sequence
<220> FEATURE:
<223> OTHER INFORMATION: Nucleophosmin/B23 Peptide

<400> SEQUENCE: 51

Val Val Leu Arg Leu Lys Cys Gly Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Histone H2A Peptide

<400> SEQUENCE: 52

Met Ser Gly Arg Gly Lys Gln Gly Gly
1               5

<210> SEQ ID NO 53
<211> LENGTH: 9
<212> TYPE: PRT
<213> ORGANISM: Artificial Sequence
<220> FEATURE:
<223> OTHER INFORMATION: Histone H2A Peptide

<400> SEQUENCE: 53

Tyr Ser Glu Arg Val Gly Ala Gly Ala
1               5

<210> SEQ ID NO 54
<211> LENGTH: 9
<212> TYPE: PRT
<213> ORGANISM: Artificial Sequence
<220> FEATURE:
<223> OTHER INFORMATION: Histone H2A Peptide

<400> SEQUENCE: 54

Ile Ile Pro Arg His Leu Gln Leu Ala
1               5

<210> SEQ ID NO 55
<211> LENGTH: 9
<212> TYPE: PRT
<213> ORGANISM: Artificial Sequence
<220> FEATURE:
<223> OTHER INFORMATION: Histone H2A Peptide

<400> SEQUENCE: 55

Leu Ala Ile Arg Asn Asp Glu Glu Leu
1               5

<210> SEQ ID NO 56
<211> LENGTH: 9
<212> TYPE: PRT
<213> ORGANISM: Artificial Sequence
<220> FEATURE:
<223> OTHER INFORMATION: Histone H2A Peptide
```

```
<400> SEQUENCE: 56

Leu Leu Gly Arg Val Thr Ile Ala Gln
1               5

<210> SEQ ID NO 57
<211> LENGTH: 9
<212> TYPE: PRT
<213> ORGANISM: Artificial Sequence
<220> FEATURE:
<223> OTHER INFORMATION: Histone H4 Peptide

<400> SEQUENCE: 57

Met Ser Gly Arg Gly Lys Gly Gly Lys
1               5

<210> SEQ ID NO 58
<211> LENGTH: 9
<212> TYPE: PRT
<213> ORGANISM: Artificial Sequence
<220> FEATURE:
<223> OTHER INFORMATION: Histone H4 Peptide

<400> SEQUENCE: 58

Leu Ala Arg Arg Gly Gly Val Lys Arg
1               5

<210> SEQ ID NO 59
<211> LENGTH: 9
<212> TYPE: PRT
<213> ORGANISM: Artificial Sequence
<220> FEATURE:
<223> OTHER INFORMATION: Histone H3 Peptide

<400> SEQUENCE: 59

Val Ala Leu Arg Glu Ile Arg Arg Tyr
1               5

<210> SEQ ID NO 60
<211> LENGTH: 9
<212> TYPE: PRT
<213> ORGANISM: Artificial Sequence
<220> FEATURE:
<223> OTHER INFORMATION: Histone H3 Peptide

<400> SEQUENCE: 60

Leu Leu Ile Arg Lys Leu Pro Phe Gln
1               5

<210> SEQ ID NO 61
<211> LENGTH: 9
<212> TYPE: PRT
<213> ORGANISM: Artificial Sequence
<220> FEATURE:
<223> OTHER INFORMATION: Histone H3 Peptide

<400> SEQUENCE: 61

Leu Ala Arg Arg Ile Arg Gly Glu Arg
1               5

<210> SEQ ID NO 62
<211> LENGTH: 13
<212> TYPE: PRT
<213> ORGANISM: Human

<400> SEQUENCE: 62
```

-continued

Ala Gly Trp Leu Ala Asp Arg Ser Val Arg Tyr Pro Ile
1               5                   10

<210> SEQ ID NO 63
<211> LENGTH: 13
<212> TYPE: PRT
<213> ORGANISM: Human

<400> SEQUENCE: 63

Ala Gly Trp Leu Ala Arg Arg Ser Val Arg Tyr Pro Ile
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is Cit

<400> SEQUENCE: 64

Ala Gly Trp Leu Ala Xaa Arg Ser Val Arg Tyr Pro Ile
1               5                   10

<210> SEQ ID NO 65
<211> LENGTH: 13
<212> TYPE: PRT
<213> ORGANISM: Human

<400> SEQUENCE: 65

Ser Ala Val Arg Ala Arg Ser Ser Val Pro Gly Val Arg
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is Cit

<400> SEQUENCE: 66

Ser Ala Val Arg Ala Xaa Ser Ser Val Pro Gly Val Arg
1               5                   10

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
ccagccaaga agaaatccac                                           20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
acagctctgg ttggcttcac                                               20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
tcctgctggt gaactgtgac                                               20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
acccaagact acgctgcact                                               20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ggctcattac cctcaccatc                                               20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
agcttgcact tggctttcat                                               20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
tggacgagtt cctgagcttt                                               20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
gtcgatgcat ctctccacaa                                               20

<210> SEQ ID NO 75
<211> LENGTH: 20

```
<212> TYPE: DNA
<213> ORGANISM: Artificial Sequence
<220> FEATURE:
<223> OTHER INFORMATION: Primer

<400> SEQUENCE: 75
gctgttcgaa gggatcaaga                                               20

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
cttccctagc accagcatgt                                               20

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
gcaggacatg tctccaatga                                               20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
agctccaggc aatacgagaa                                               20

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
gcgacactgt tcgaaggact                                               20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
ggccttagag ttccctctgg                                               20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
```
ccttcttccc aaacatggtg                                         20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
atgtgccacc acttgaaggt                                         20

<210> SEQ ID NO 83
<211> LENGTH: 19
<212> TYPE: DNA
<213> ORGANISM: Artificial Sequence
<220> FEATURE:
<223> OTHER INFORMATION: Primer

<400> SEQUENCE: 83
ggttcagatt tcatactac                                          19

<210> SEQ ID NO 84
<211> LENGTH: 19
<212> TYPE: DNA
<213> ORGANISM: Artificial Sequence
<220> FEATURE:
<223> OTHER INFORMATION: Primer

<400> SEQUENCE: 84
accagagctg tgaaagatc                                          19

<210> SEQ ID NO 85
<211> LENGTH: 19
<212> TYPE: DNA
<213> ORGANISM: Artificial Sequence
<220> FEATURE:
<223> OTHER INFORMATION: Primer

<400> SEQUENCE: 85
ccagagctgt gaaagatca                                          19

<210> SEQ ID NO 86
<211> LENGTH: 19
<212> TYPE: DNA
<213> ORGANISM: Artificial Sequence
<220> FEATURE:
<223> OTHER INFORMATION: Primer

<400> SEQUENCE: 86
ctgcgaggat gatgaagtg                                          19

<210> SEQ ID NO 87
<211> LENGTH: 19
<212> TYPE: DNA
<213> ORGANISM: Artificial Sequence
<220> FEATURE:
<223> OTHER INFORMATION: Primer

<400> SEQUENCE: 87
ggtgtacgcg tgcagtatt                                          19

<210> SEQ ID NO 88
<211> LENGTH: 19
<212> TYPE: DNA
<213> ORGANISM: Artificial Sequence

```
<220> FEATURE:
<223> OTHER INFORMATION: Primer

<400> SEQUENCE: 88
ctactctggc catgaaagc                                                  19

<210> SEQ ID NO 89
<211> LENGTH: 19
<212> TYPE: DNA
<213> ORGANISM: Artificial Sequence
<220> FEATURE:
<223> OTHER INFORMATION: Primer

<400> SEQUENCE: 89
ggtcctgcta caaactgtt                                                  19

<210> SEQ ID NO 90
<211> LENGTH: 19
<212> TYPE: DNA
<213> ORGANISM: Artificial Sequence
<220> FEATURE:
<223> OTHER INFORMATION: Primer

<400> SEQUENCE: 90
gttctctaag gcggaagct                                                  19

<210> SEQ ID NO 91
<211> LENGTH: 19
<212> TYPE: DNA
<213> ORGANISM: Artificial Sequence
<220> FEATURE:
<223> OTHER INFORMATION: Primer

<400> SEQUENCE: 91
agatgaacaa agtgagagt                                                  19

<210> SEQ ID NO 92
<211> LENGTH: 19
<212> TYPE: DNA
<213> ORGANISM: Artificial Sequence
<220> FEATURE:
<223> OTHER INFORMATION: Primer

<400> SEQUENCE: 92
gacaatcaat gaaattctg                                                  19

<210> SEQ ID NO 93
<211> LENGTH: 19
<212> TYPE: DNA
<213> ORGANISM: Artificial Sequence
<220> FEATURE:
<223> OTHER INFORMATION: Primer

<400> SEQUENCE: 93
tcaacgactt ctacaccta                                                  19

<210> SEQ ID NO 94
<211> LENGTH: 19
<212> TYPE: DNA
<213> ORGANISM: Artificial Sequence
<220> FEATURE:
<223> OTHER INFORMATION: Primer

<400> SEQUENCE: 94
cgtacgcgga atacttcga                                                  19
```

<210> SEQ ID NO 95
<211> LENGTH: 19
<212> TYPE: DNA
<213> ORGANISM: Artificial Sequence
<220> FEATURE:
<223> OTHER INFORMATION: Primer

<400> SEQUENCE: 95
cgtacgcgga atacttcga                                                19

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
catggtctac aaccgcacac                                               20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
cctgtgattg tcccggtcac                                               20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
ccggatacga gatagttctg                                               20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
atcctggatc cagcgatcgc                                               20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
cctatgcggt gctctacctc                                               20

<210> SEQ ID NO 101
<211> LENGTH: 20
<212> TYPE: DNA
<213> ORGANISM: Artificial Sequence
<220> FEATURE:
<223> OTHER INFORMATION: Primer

```
<400> SEQUENCE: 101
cagctcggat catcacggtc                                                  20

<210> SEQ ID NO 102
<211> LENGTH: 24
<212> TYPE: DNA
<213> ORGANISM: Artificial Sequence
<220> FEATURE:
<223> OTHER INFORMATION: Primer

<400> SEQUENCE: 102
ccacccatgg caaattccat ggca                                             24

<210> SEQ ID NO 103
<211> LENGTH: 24
<212> TYPE: DNA
<213> ORGANISM: Artificial Sequence
<220> FEATURE:
<223> OTHER INFORMATION: Primer

<400> SEQUENCE: 103
tctagacggc aggtcaggtc cacc                                             24

<210> SEQ ID NO 104
<211> LENGTH: 16
<212> TYPE: DNA
<213> ORGANISM: Artificial Sequence
<220> FEATURE:
<223> OTHER INFORMATION: Primer

<400> SEQUENCE: 104
tgctaaccat ttgaag                                                      16

<210> SEQ ID NO 105
<211> LENGTH: 18
<212> TYPE: DNA
<213> ORGANISM: Artificial Sequence
<220> FEATURE:
<223> OTHER INFORMATION: Primer

<400> SEQUENCE: 105
ttgtcattgc ggccgtgg                                                    18

<210> SEQ ID NO 106
<211> LENGTH: 18
<212> TYPE: DNA
<213> ORGANISM: Artificial Sequence
<220> FEATURE:
<223> OTHER INFORMATION: Primer

<400> SEQUENCE: 106
catgtctcag atgatcct                                                    18

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
cacacttata ggcctcacag                                                  20

<210> SEQ ID NO 108
```

```
<211> LENGTH: 25
<212> TYPE: DNA
<213> ORGANISM: Artificial Sequence
<220> FEATURE:
<223> OTHER INFORMATION: Primer

<400> SEQUENCE: 108
tgatgacatc aagaaggtgg tgaag                                              25

<210> SEQ ID NO 109
<211> LENGTH: 23
<212> TYPE: DNA
<213> ORGANISM: Artificial Sequence
<220> FEATURE:
<223> OTHER INFORMATION: Primer

<400> SEQUENCE: 109
tccttggagg ccatgtaggc cat                                                23
```